United States Patent
Kaler

(10) Patent No.: US 12,173,306 B2
(45) Date of Patent: *Dec. 24, 2024

(54) CODON-OPTIMIZED REDUCED-SIZE ATP7A CDNA AND USES FOR TREATMENT OF COPPER TRANSPORT DISORDERS

(71) Applicant: The United States of America, as represented by the Secretary, Dept. of Health and Human Services, Bethesda, MD (US)

(72) Inventor: Stephen G. Kaler, Bethesda, MD (US)

(73) Assignee: The United States of America, as represented by the Secretary, Dept. of Health and Human Services, Bethesda, MD (US)

( * ) Notice: Subject to any disclaimer, the term of this patent is extended or adjusted under 35 U.S.C. 154(b) by 398 days.

This patent is subject to a terminal disclaimer.

(21) Appl. No.: 17/217,961

(22) Filed: Mar. 30, 2021

(65) Prior Publication Data

US 2021/0214751 A1   Jul. 15, 2021

Related U.S. Application Data

(63) Continuation of application No. 15/769,294, filed as application No. PCT/US2016/058124 on Oct. 21, 2016, now Pat. No. 10,988,778.

(60) Provisional application No. 62/244,594, filed on Oct. 21, 2015.

(51) Int. Cl.
| | |
|---|---|
| *A61K 48/00* | (2006.01) |
| *A61K 33/34* | (2006.01) |
| *A61K 38/46* | (2006.01) |
| *A61P 3/00* | (2006.01) |
| *A61P 25/00* | (2006.01) |
| *C12N 9/14* | (2006.01) |
| *C12N 15/86* | (2006.01) |

(52) U.S. Cl.
CPC .............. *C12N 15/86* (2013.01); *A61K 33/34* (2013.01); *A61K 38/46* (2013.01); *A61K 48/005* (2013.01); *A61P 3/00* (2018.01); *A61P 25/00* (2018.01); *C12N 9/14* (2013.01); *C12Y 306/03004* (2013.01); *C12N 2800/22* (2013.01)

(58) Field of Classification Search
None
See application file for complete search history.

(56) References Cited

U.S. PATENT DOCUMENTS

| | | | | |
|---|---|---|---|---|
| 6,812,339 | B1* | 11/2004 | Venter | C12Q 1/6883 536/23.1 |
| 2009/0175860 | A1 | 7/2009 | Stover et al. | |
| 2010/0240739 | A1* | 9/2010 | Barkats | A61P 25/00 514/44 R |
| 2012/0177605 | A1* | 7/2012 | Kaspar | A61K 48/005 435/320.1 |
| 2013/0259923 | A1 | 10/2013 | Bancel et al. | |
| 2015/0111955 | A1* | 4/2015 | High | C12N 15/86 435/456 |

FOREIGN PATENT DOCUMENTS

| | | | | |
|---|---|---|---|---|
| WO | WO 2010/042102 | | 4/2010 | |
| WO | WO-2013151666 A2 * | | 10/2013 | A61K 38/17 |

OTHER PUBLICATIONS

Thomas Nature review Genetics, 4(5):346-58 (Year: 2003).*
Simonato et al Nat Rev Neurol. May; 9(5): 277-291 (Year: 2013).*
Shevtsova et al Exp Physiol. 90.1, 53-59 (Year: 2005).*
Haddad et al Molecular Therapy vol. 23, Supplement 1, , S78 (Year: 2015).*
Kaler et al Nat Rev Neurol. 17(1): 15-29 (Year: 2011).*
Hsich et al. Hum. Gene Ther. 13: 579-604, (Year: 2002).*
Donsante et al (Molecular Therapy, 19, 12, 2114-2123 (Year: 2011).*
Nakamura et al (Nucleic Acids Res. 28:292, (Year: 2000).*
Sheela et al Clin Genet. Sep;68(3):278-83 (Year: 2005).*
Haddad Molecular Therapy, 10, 165-178 (Year: 2018).*
Murlidharan et al Frontiers in Molecular Neuroscience, 1-9 (Year: 2014).*
Manfredsson Mol. Therapy, 17, 403-405 (Year: 2009).*
Genbank Accession No. AAA35580.1, May 7, 1993 (3 pages).
Genbank Accession No. BC156437.1, Aug. 4, 2008 (3 pages).
Bali et al., "Decoding mechanisms by which silent codon changes influence protein biogenesis and function," *Int. J. Biochem. Cell Biol.*, vol. 64, pp. 58-74, 2015.
Database EMBL Accession No. LF443811, Oct. 29, 2016 (2 pages).
Database Geneseq Accession No. AEH10411, Jun. 11, 2007 (2 pages).
Database Geneseq Accession No. BCE94264, Nov. 19, 2015 (2 pages).
Donsante et al., "ATP7 A Gene Addition to the Choroid Plexus Results in Long-term Rescue of the Lethal Copper Transport Defect in a Menkes Disease Mouse Model," *Molecular Therapy*, vol. 19, No. 12, pp. 2114-2123, 2011.
Elena et al., "Expression of codon optimized genes in microbial systems: current industrial applications and perspectives," *Front. Microbiol.*, vol. 5, Article 21, 2014 (8 pages).

(Continued)

*Primary Examiner* — Anoop K Singh
(74) *Attorney, Agent, or Firm* — Klarquist Sparkman, LLP

(57) ABSTRACT

Disclosed herein are codon-optimized nucleic acids encoding a reduced-size ATP7A protein. Also disclosed are vectors and recombinant viruses (such as recombinant adeno-associated viruses) including the codon-optimized nucleic acids encoding the reduced-size ATP7A protein and compositions including the disclosed vectors and viruses. Further disclosed herein are methods of treating copper transport disorders, for example by administering a disclosed nucleic acid, vector, or recombinant virus to a subject with a copper transport disorder, such as Menkes disease, occipital horn syndrome, or ATP7A-related distal motor neuropathy.

9 Claims, 7 Drawing Sheets
Specification includes a Sequence Listing.

(56) References Cited

OTHER PUBLICATIONS

Fedorova et al., "Hemagglutinin Codon Optimization: a Promising Tool for Enhancing the Immunogenicity of Influenza Virus Vaccines," *Molecular Genetics, Microbiology and Virology*, vol. 29, No. 4, pp. 159-166, 2014.
Goodman & Gilman's The Pharmacological basis of Therapeutics, McGraw-Hill, New York, NY, pp. 77-101, 1996.
Haddad et al., "High-Resolution X-Ray Fluorescence Microscopy (XFM) Indicates Enhanced Brain Copper Delivery in AAV9-Treated Menkes Disease Mice," Molecular Therapy, vol. 24, Suppl. 1, pp. S142-S143, 2016.
Haddad et al., "Survival, Growth, and Neurobehavioral Outcomes in a Mouse Model of Menkes Disease With CSF-Directed AAV9 and Subcutaneous Copper Histidine," *Molecular Therapy*, vol. 23, Suppl. 1, p. S78, 2015.
Hsich et al., "Critical Issues in Gene Therapy for Neurologic Disease," *Human Gene Therapy*, vol. 13, pp. 570-604, 2002.
Husain et al. "Long-term AAV vector gene and protein expression in mouse brain from a small pan-cellular promoter is similar to neural cell promoters," *Gene Therapy*, vol. 16, pp. 927-932, 2009.
Kaler et al., "Neonatal Diagnosis and Treatment of Menkes Disease," *New England Journal of Medicine*, vol. 358, No. 6, pp. 605-614, 2008.
Kaler et al., "Occipital horn syndrome and a mild Menkes phenotype associated with splice site mutations and the *MNK* locus," *Nat. Genetics*, vol. 8, pp. 195-202, 1994.
Kaler et al., "Successful Early Copper Therapy in Menkes Disease Associated with a Mutant Transcript Containing a Small In-Frame Deletion," *Biochemical Mol. Med.*, vol. 57, pp. 37-46, 1996.
Kaler, "ATP7A-related copper transport diseases—emerging concepts and future trends," Nat. Rev. Neurol. vol. 7, pp. 15-29, 2011.
Kaler, "Inborn errors of copper metabolism," Chapter 180, *Handbook of Clin. Neurol.*, vol. 113 ($3^{rd}$ series), pp. 1745-1754, 2013.
Kaler, "Menkes disease mutations and response to early copper histidine treatment," *Nature Genetics*, vol. 13, pp. 21-22, 1996.
Kaler, "Neurodevelopment and brain growth in classic Menkes disease is influenced by age and symptomatology at initiation of copper treatment," *Journal of Trace Elements in Medicine and Biology*, vol. 28, No. 4, pp. 427-430, 2014.
Liu et al., "Downregulation of myelination, energy, and translational genes in Menkes disease brain," *Mol. Genet. Metab.*, vol. 85, pp. 291-300, 2005.
Nakamura et al., "Codon usage tabulated from international DNA sequence databases: status for the year 2000," *Nucleic Acids Research*, vol. 28, p. 292, 2000.
Sheela et al., "Copper-replacement treatment for symptomatic Menkes disease: ethical considerations," *Clin. Genet.*, vol. 68, No. 3, pp. 278-283, 2005.
Shevtsova et al., "Promoters and serotypes: targeting of adeno-associated virus vectors for gene transfer in the rat central nervous system in vitro and in vivo," *Experimental Physiology*, vol. 90, No. 1, pp. 53-59, 2005.
Simonato et al., "Progress in gene therapy for neurological disorders," *Nat. Rev. Neurol.*, vol. 9, No. 5, pp. 277-291, 2013.
Tang et al., "Clinical outcomes in Menkes disease patients with a copper-responsive ATP7A mutation, G727R," *Mol. Genet. Metab.* vol. 95, No. 3, pp. 174-181, 2008 (19 pages, Author Manuscript version).

\* cited by examiner

FIG. 2D
```
co_rsATP7A  2997  C  GC  CC C A C AGT  T  CAG  C    CC  AT    TTCC  G  C
nat_rsATP7A 2997  T  C A  CC C T A  TCA A  GTC  T     CC     CAGT   T
```
```
co_rsATP7A  3057  TTC  CA  C C  AT AGC A TAGC  GC  CC CC GACAC  TC  CA C CACAC A
nat_rsATP7A 3057  CAG  CA   T  C A GC  CTCA  C  CC CC GACAC  CA   C  T CA CAC  T
```
```
co_rsATP7A  3117  TC
nat_rsATP7A 3117  AT
```
FIG. 3
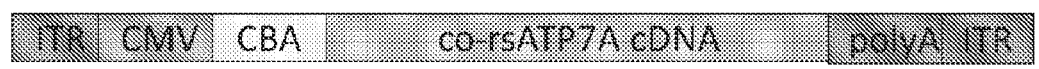
FIG. 4
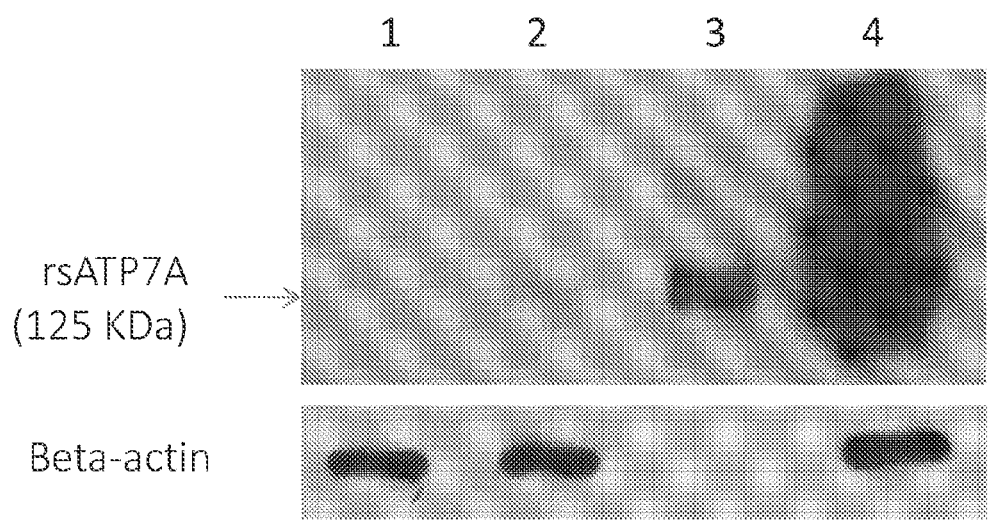

SEQUENCE LISTING

```
<160> NUMBER OF SEQ ID NOS: 3

<210> SEQ ID NO 1
<211> LENGTH: 3120
<212> TYPE: DNA
<213> ORGANISM: Artificial Sequence
<220> FEATURE:
<223> OTHER INFORMATION: codon-optimized reduced-size ATP7A cDNA

<400> SEQUENCE: 1
atgccacttc tcacgagcac taacgagttc tacacgaagg gaatgacgcc cgtgcaggac      60
aaagaggaag gaaaaaatag ctcaaaatgt tatattcagg tgaccgggat gacatgcgcg     120
tcctgcgtcg caaatatcga gaggaacctg cggcgggaag aagggatcta cagtatcctc     180
gtggcactga tggcaggtaa ggccgaagtt cgatacaacc cagctgttat ccaaccccca     240
atgattgcag agtttatccg agaactgggg ttcggggcga cggtgatcga gaacgccgac     300
gaaggcgatg gagtcttgga acttgtggta aggggcatga catgtgcaag ctgtgtacat     360
aagatcgaga gctctcttac aaagcatagg ggtattctgt attgctctgt ggccctggcg     420
actaacaagg cacacatcaa gtacgatccc gagatcattg gccccaggga cattatacat     480
actattgaaa gcctcggctt cgaggcctct ctggtcaaga aggatcgaag cgccagccat     540
ttggaccata agagagagat ccggcagtgg agaaggagct tcctggtttc tctgtttttc     600
tgtatccctg tgatgggcct tatgacatat atgatggtaa tggaccatca ctttgccacc     660
ctccaccata accagaatat gtcaaaagag gaaatgatca accttcactc ctccatgttc     720
ctcgagcgcc aaatttttgcc cggcttgagc gtgatgaacc tgctgtcatt cctcctgtgc     780
gtgccagtgc agttttttcgg cgggtggtat ttctatattc aggcctacaa agctctgaag     840
cacaagacag caaatatgga cgtgcttatc gtccttgcta ccacaattgc attcgcatac     900
tccctgatta ttttgttggt cgctatgtac gagagggcca aagttaaccc tatcacattc     960
tttgacaccc cccccatgct gttcgtattt atcgcgctcg gccgctggtt ggagcatata    1020
gcaaagggca agacatccga agccctggca aagctgattt ctctccaagc gacagaggct    1080
```

```
accattgtga ccctcgacag cgacaacatc ctgctctctg aagagcaagt ggacgttgaa    1140
ctggtgcaga gggggatat catcaaagtg gtccccggcg ggaagttcc tgtggatggc       1200 cgagtgatcg agggtcattc tatggtggac gaatcactga ttactggcga agcaatgcct    1260
gtggcaaaaa aacccgggag caccgtaatt gctgggagta caaccagaa cggaagcctg     1320 ttgatttgtg ccacgcatgt aggagccgat acaactctca gccagattgt gaagttggtg   1380
gaggaagcac agactagcaa ggctccgatc cagcaattcg cagataagct tagtgggtac    1440
tttgtcccat tcatagtgtt cgtgtcaatt gccaccctgc tggtctggat tgtcattggc    1500
ttcctgaact tcgagatcgt ggaaacctat ttccccgggt acaaccggtc tatcagtcgc    1560
acagaaacaa tcattagatt tgcctttcag gctagtatca ctgtgctttg catcgcctgc    1620
ccatgtagcc tgggcctggc caccccctacc gcagtcatgg ttgggaccgg agttggggcc   1680
cagaatggga ttcttatcaa aggtggcgaa ccactggaga tggcgcataa agtcaaggtc    1740
gtggtgtttg acaagaccgg tacgattacc catggaacgc cggtcgtgaa tcaggtgaag    1800
gtcctgactg agagcaatcg aatttcacat cacaagattt tggcaatcgt gggtaccgcc    1860
gagagcaaca gtgagcatcc actgggaaca gcaataacca gtattgtaa gcaagaactg      1920 gacacggaaa cgctgggaac atgtattgac ttccaggtgg tccctggatg tggcattagt    1980
tgcaaggtca caaacatcga aggactcctt cacaagaata actggaatat cgaggataat    2040
aatatcaaga acgcatcctt ggtgcagatt gacgcttcaa acgagcagag ctctaccagt   2100
agtagcatga tcattgatgc gcagataagc aacgcccta acgcacagca acataaggtc     2160
ctgataggga atagagagtg gatgatcagg aacggactgg tcatcaataa cgacgtcaat  2220
gacttcatga ccgaacacga gcgaaaaggg aggacagccg tccttgtcgc tgtcgatgac   2280
gagctgtgtg gactgatcgc aatcgccgat acggtaaaac cagaggccga gcttgccata  2340
cacattctga gtcaatggg actggaagtg gtgctgatga ccggggataa cagcaagacc    2400
gcccgaagta ttgcaagcca ggtgggcatc accaaggtct tcgccgaagt gctgccgagc    2460
cataaagtgg ccaaggtgaa gcagctgcag gaagagggca gcgggtggc aatggtgggc      2520 gacggaatca acgactcacc cgcgctggca atggccaatg tggggatcgc cattggaaca    2580
gggacagatg tggccatcga agccgccgac gtcgtgctga taaggaatga cttgttggac     2640
gtagtcgcat ccattgatct gtctaggaag acagttaaac gcatcagaat taatttcgtg   2700
tttgcgctga tctataatct cgtcggtatc cctattgccg ctggcgtgtt tatgcctatc    2760
gggctggtgt tgcagccatg gatgggctca gctgctatgg ccgccagcag tgtatctgtg   2820
gtcttgagca gcttgttttt gaaactgtat cgcaagccga catatgaaag ctacgaactg   2880
cctgccagga gtcagatagg acagaaatca cccagcgaga tatctgttca tgtgggaatt    2940
gatgatacaa gtcggaatag cccccaaattg ggcttgctgg accgcattgt caactacagc   3000
cgagcctcta tcaacagtct tctcagtgac aagcgctcat tgaattccgt ggtgacttct    3060
gagcccgata agcatagcct gctggtggga gactttcggg aggacgatga cacagctctg     3120
```

<210> SEQ ID NO 2
<211> LENGTH: 1040
<212> TYPE: PRT
<213> ORGANISM: Artificial Sequence
<220> FEATURE:
<223> OTHER INFORMATION: reduced-size ATP7A protein

<400> SEQUENCE: 2

```
Met Pro Leu Leu Thr Ser Thr Asn Glu Phe Tyr Thr Lys Gly Met Thr
1               5                   10                  15

Pro Val Gln Asp Lys Glu Glu Gly Lys Asn Ser Ser Lys Cys Tyr Ile
                20                  25                  30

Gln Val Thr Gly Met Thr Cys Ala Ser Cys Val Ala Asn Ile Glu Arg
            35                  40                  45

Asn Leu Arg Arg Glu Glu Gly Ile Tyr Ser Ile Leu Val Ala Leu Met
        50                  55                  60

Ala Gly Lys Ala Glu Val Arg Tyr Asn Pro Ala Val Ile Gln Pro Pro
65                  70                  75                  80

Met Ile Ala Glu Phe Ile Arg Glu Leu Gly Phe Gly Ala Thr Val Ile
                85                  90                  95

Glu Asn Ala Asp Glu Gly Asp Gly Val Leu Glu Leu Val Val Arg Gly
                100                 105                 110

Met Thr Cys Ala Ser Cys Val His Lys Ile Glu Ser Ser Leu Thr Lys
            115                 120                 125

His Arg Gly Ile Leu Tyr Cys Ser Val Ala Leu Ala Thr Asn Lys Ala
        130                 135                 140

His Ile Lys Tyr Asp Pro Glu Ile Ile Gly Pro Arg Asp Ile Ile His
145                 150                 155                 160

Thr Ile Glu Ser Leu Gly Phe Glu Ala Ser Leu Val Lys Lys Asp Arg
                165                 170                 175

Ser Ala Ser His Leu Asp His Lys Arg Glu Ile Arg Gln Trp Arg Arg
            180                 185                 190

Ser Phe Leu Val Ser Leu Phe Phe Cys Ile Pro Val Met Gly Leu Met
        195                 200                 205

Thr Tyr Met Met Val Met Asp His His Phe Ala Thr Leu His His Asn
210                 215                 220

Gln Asn Met Ser Lys Glu Glu Met Ile Asn Leu His Ser Ser Met Phe
225                 230                 235                 240

Leu Glu Arg Gln Ile Leu Pro Gly Leu Ser Val Met Asn Leu Leu Ser
                245                 250                 255

Phe Leu Leu Cys Val Pro Val Gln Phe Phe Gly Gly Trp Tyr Phe Tyr
            260                 265                 270

Ile Gln Ala Tyr Lys Ala Leu Lys His Lys Thr Ala Asn Met Asp Val
        275                 280                 285

Leu Ile Val Leu Ala Thr Thr Ile Ala Phe Ala Tyr Ser Leu Ile Ile
290                 295                 300

Leu Leu Val Ala Met Tyr Glu Arg Ala Lys Val Asn Pro Ile Thr Phe
305                 310                 315                 320

Phe Asp Thr Pro Pro Met Leu Phe Val Phe Ile Ala Leu Gly Arg Trp
                325                 330                 335

Leu Glu His Ile Ala Lys Gly Lys Thr Ser Glu Ala Leu Ala Lys Leu
            340                 345                 350

Ile Ser Leu Gln Ala Thr Glu Ala Thr Ile Val Thr Leu Asp Ser Asp
        355                 360                 365

Asn Ile Leu Leu Ser Glu Glu Gln Val Asp Val Glu Leu Val Gln Arg
370                 375                 380

Gly Asp Ile Ile Lys Val Val Pro Gly Gly Lys Phe Pro Val Asp Gly
385                 390                 395                 400

Arg Val Ile Glu Gly His Ser Met Val Asp Glu Ser Leu Ile Thr Gly
                405                 410                 415

Glu Ala Met Pro Val Ala Lys Lys Pro Gly Ser Thr Val Ile Ala Gly
```

-continued

```
                420                 425                 430
    Ser Ile Asn Gln Asn Gly Ser Leu Leu Ile Cys Ala Thr His Val Gly
                    435                 440                 445

Ala Asp Thr Thr Leu Ser Gln Ile Val Lys Leu Val Glu Glu Ala Gln
        450                 455                 460

Thr Ser Lys Ala Pro Ile Gln Gln Phe Ala Asp Lys Leu Ser Gly Tyr
    465                 470                 475                 480

Phe Val Pro Phe Ile Val Phe Val Ser Ile Ala Thr Leu Leu Val Trp
                        485                 490                 495

Ile Val Ile Gly Phe Leu Asn Phe Glu Ile Val Glu Thr Tyr Phe Pro
                    500                 505                 510

Gly Tyr Asn Arg Ser Ile Ser Arg Thr Glu Thr Ile Ile Arg Phe Ala
                515                 520                 525

Phe Gln Ala Ser Ile Thr Val Leu Cys Ile Ala Cys Pro Cys Ser Leu
            530                 535                 540

Gly Leu Ala Thr Pro Thr Ala Val Met Val Gly Thr Gly Val Gly Ala
    545                 550                 555                 560

Gln Asn Gly Ile Leu Ile Lys Gly Gly Glu Pro Leu Glu Met Ala His
                        565                 570                 575

Lys Val Lys Val Val Phe Asp Lys Thr Gly Thr Ile Thr His Gly
                    580                 585                 590

Thr Pro Val Val Asn Gln Val Lys Val Leu Thr Glu Ser Asn Arg Ile
                595                 600                 605

Ser His His Lys Ile Leu Ala Ile Val Gly Thr Ala Glu Ser Asn Ser
            610                 615                 620

Glu His Pro Leu Gly Thr Ala Ile Thr Lys Tyr Cys Lys Gln Glu Leu
    625                 630                 635                 640

Asp Thr Glu Thr Leu Gly Thr Cys Ile Asp Phe Gln Val Val Pro Gly
                        645                 650                 655

Cys Gly Ile Ser Cys Lys Val Thr Asn Ile Glu Gly Leu Leu His Lys
                    660                 665                 670

Asn Asn Trp Asn Ile Glu Asp Asn Asn Ile Lys Asn Ala Ser Leu Val
                675                 680                 685

Gln Ile Asp Ala Ser Asn Glu Gln Ser Ser Thr Ser Ser Ser Met Ile
            690                 695                 700

Ile Asp Ala Gln Ile Ser Asn Ala Leu Asn Ala Gln Gln His Lys Val
    705                 710                 715                 720

Leu Ile Gly Asn Arg Glu Trp Met Ile Arg Asn Gly Leu Val Ile Asn
                        725                 730                 735

Asn Asp Val Asn Asp Phe Met Thr Glu His Glu Arg Lys Gly Arg Thr
                    740                 745                 750

Ala Val Leu Val Ala Val Asp Asp Glu Leu Cys Gly Leu Ile Ala Ile
                755                 760                 765

Ala Asp Thr Val Lys Pro Glu Ala Glu Leu Ala Ile His Ile Leu Lys
            770                 775                 780

Ser Met Gly Leu Glu Val Val Leu Met Thr Gly Asp Asn Ser Lys Thr
    785                 790                 795                 800

Ala Arg Ser Ile Ala Ser Gln Val Gly Ile Thr Lys Val Phe Ala Glu
                        805                 810                 815

Val Leu Pro Ser His Lys Val Ala Lys Val Lys Gln Leu Gln Glu Glu
                    820                 825                 830

Gly Lys Arg Val Ala Met Val Gly Asp Gly Ile Asn Asp Ser Pro Ala
                835                 840                 845
```

```
Leu Ala Met Ala Asn Val Gly Ile Ala Ile Gly Thr Gly Thr Asp Val
    850                 855                 860

Ala Ile Glu Ala Ala Asp Val Val Leu Ile Arg Asn Asp Leu Leu Asp
865                 870                 875                 880

Val Val Ala Ser Ile Asp Leu Ser Arg Lys Thr Val Lys Arg Ile Arg
                885                 890                 895

Ile Asn Phe Val Phe Ala Leu Ile Tyr Asn Leu Val Gly Ile Pro Ile
                900                 905                 910

Ala Ala Gly Val Phe Met Pro Ile Gly Leu Val Leu Gln Pro Trp Met
            915                 920                 925

Gly Ser Ala Ala Met Ala Ala Ser Ser Val Ser Val Val Leu Ser Ser
    930                 935                 940

Leu Phe Leu Lys Leu Tyr Arg Lys Pro Thr Tyr Glu Ser Tyr Glu Leu
945                 950                 955                 960

Pro Ala Arg Ser Gln Ile Gly Gln Lys Ser Pro Ser Glu Ile Ser Val
                965                 970                 975

His Val Gly Ile Asp Asp Thr Ser Arg Asn Ser Pro Lys Leu Gly Leu
                980                 985                 990

Leu Asp Arg Ile Val Asn Tyr Ser Arg Ala Ser Ile Asn Ser Leu Leu
                995                 1000                1005

Ser Asp Lys Arg Ser Leu Asn Ser Val Val Thr Ser Glu Pro Asp
    1010                1015                1020

Lys His Ser Leu Leu Val Gly Asp Phe Arg Glu Asp Asp Thr
    1025                1030                1035

Ala Leu
    1040

<210> SEQ ID NO 3
<211> LENGTH: 3120
<212> TYPE: DNA
<213> ORGANISM: Artificial Sequence
<220> FEATURE:
<223> OTHER INFORMATION: reduced-size ATP7A cDNA

<400> SEQUENCE: 3
atgccgcttt tgacttcaac taatgaattt tatactaaag ggatgacacc agttcaagac      60
aaggaggaag gaaagaattc atctaagtgt tacatacagg tcactggcat gacttgcgct     120
tcctgtgtag caaacattga acggaattta aggcgggaag aaggaatata ttctatactt     180
gtggccctga tggctggcaa ggcagaagta aggtataatc ctgctgttat acaaccccca     240
atgatagcag agttcatccg agaacttgga tttggagcca ctgtgataga aatgctgat      300 gaaggagatg tgttttggaa acttgttgtg aggggaatga cgtgtgcctc ctgcgtacat     360
aaaatagagt ctagtctcac aaaacacaga gggatcctat actgctccgt ggccctggca     420
accaacaaag cacatattaa atatgaccca gaattattg gtcctagaga tattatccat      480
acaattgaaa gcttaggttt tgaagcttct ttggtcaaga aggatcggtc agcaagtcac     540
ttagatcata acgagaaat aagacaatgg agacggtctt ttcttgtgag tctgtttttc      600
tgtattcctg taatggggct gatgatatat atgatggtta tggaccacca ctttgcaact     660
cttcaccata atcaaaacat gagtaaagaa gaaatgatca accttcattc ttctatgttc     720
ctggagcgcc agattcttcc aggattgtct gttatgaatt tgctgtccctt tttattgtgt    780 gtacctgtac agtttttcgg aggctggtac ttctacattc aggcttataa agcactgaag     840
cataagacag caaatatgga cgtactgatt gtgctggcaa ccaccattgc atttgcctac     900
```

```
tctttgatta ttcttctagt tgcaatgtat gagagagcca aagtgaaccc tattactttc    960
tttgacacac cccctatgct gtttgtgttt attgcactag gccgatggct ggaacatata   1020
gcaaagggca aaacatcaga ggctcttgca aagttaattt cactacaagc tacagaagca   1080
actattgtaa ctcttgattc tgataatatc ctcctcagtg aagaacaagt ggatgtggaa   1140
cttgtacaac gtggagatat cattaaagta gttccaggag gcaaatttcc agtggatggt   1200
cgtgttattg aaggacattc tatggtagat gagtccctca tcacagggga ggcaatgcct   1260
gtggctaaga aacctggcag cacagtgatt gctggttcca ttaaccagaa cgggtcactg   1320
cttatctgcg caacacatgt tggagcagac acaaccctt ctcaaattgt caaacttgtg   1380
gaagaggcac aaacatcaaa ggctcctatc cagcagtttg cagacaaact cagtggctat   1440
tttgttcctt ttattgtttt tgtttccatt gccaccctct ggtatggat tgtaattgga   1500 tttctgaatt ttgaaattgt ggaaacctac tttcctggct acaatagaag tatctcccga   1560
acagaaacga taatacgatt tgcttttcaa gcctctatca cagttctgtg tattgcatgt   1620
ccctgttcac tgggactggc cactccaact gctgtgatgg tgggtacagg agtaggtgct   1680
caaaatggca tactaataaa aggtggagag ccattggaga tggctcataa ggtaaaggta   1740
gtggtatttg ataagactgg aaccattact cacggaaccc cagtggtgaa tcaagtaaag   1800
gttctaactg aaagtaacag aatatcacac cataaaatct tggccattgt gggaactgct   1860
gaaagtaaca gtgaacaccc tctaggaaca gccataacca atattgcaa acaggagctg   1920 gacactgaaa ccttgggtac ctgcatagat ttccaggttg tgccaggctg tggtattagc   1980
tgtaaagtca ccaatattga aggcttgcta cataagaata actggaatat agaggacaat   2040
aatattaaaa atgcatccct ggttcaaatt gatgccagta atgaacagtc atcaacttcg   2100
tcttccatga ttattgatgc ccagatctca aatgctctta atgctcagca gtataaagtc   2160
ctcattggta accgggagtg gatgattaga aatggtcttg tcattaataa cgatgtaaat   2220
gatttcatga ctgaacatga gagaaaaggt cggactgctg tattagtagc agttgatgat   2280
gagctgtgtg gcttgatagc cattgcagac acagtgaagc ctgaagcaga actggctatc   2340
catattctga aatctatggg cttagaagta gttctgatga ctggagacaa cagtaaaaca   2400
gctagatcta ttgcttctca ggttggcatt actaaggtgt tgctgaagt tctaccttct   2460 cacaaggttg ctaaagtgaa gcaacttcaa gaggagggga acgggtagc aatggtggga   2520 gatggaatca atgactcccc agctctggca atggctaatg tgggaattgc tattggcaca   2580
ggcacagatg tagccattga agcagctgat gtggttttga taaggaatga tcttctggat   2640
gtagtggcaa gtattgactt atcaagagag acagtcaaga ggattcggat aaattttgtc   2700
tttgctctaa tttataatct ggttggaatt cccatagctg ctggagtttt tatgcccatt   2760
ggtttggttt tgcagccctg gatgggatct gcagcaatgg ctgcttcatc tgtttctgta   2820
gtactttctt ctctcttcct taaactttac aggaaaccaa cttacgagag ttatgaactg   2880
cctgcccgga gccagatagg acagaagagt ccttcagaaa tcagcgttca tgttggaata   2940 gatgataccct caaggaattc tcctaaactg ggtttgctgg accggattgt taattatagc   3000
agagcctcta taaactcact actgtctgat aaacgctccc taaacagtgt tgttaccagt   3060
gaacctgaca agcactcact cctggtggga gacttcaggg aagatgatga cactgcatta   3120
```

CODON-OPTIMIZED REDUCED-SIZE ATP7A CDNA AND USES FOR TREATMENT OF COPPER TRANSPORT DISORDERS

CROSS REFERENCE TO RELATED APPLICATION

This is a continuation of U.S. application Ser. No. 15/769,294, filed Apr. 18, 2018, which is the § 371 U.S. National Stage of International Application No. PCT/US2016/058124, filed Oct. 21, 2016, which was published in English under PCT Article 21 (2), which in turn claims the benefit of U.S. Provisional Application No. 62/244,594, filed Oct. 21, 2015, which is incorporated herein by reference in its entirety.

FIELD OF THE DISCLOSURE

This disclosure relates to codon-optimized ATP7A nucleic acids and their use in treating ATP7A-related copper transport disorders.

BACKGROUND

Copper plays a critical role in metabolism as a cofactor of key metabolic enzymes (such as dopamine β hydroxylase, lysyl oxidase, Cu/Zn superoxide dismutase, and cytochrome c oxidase). Human P-type ATPase copper-transporting ATPase 1 (ATP7A) transports copper from enterocytes (where it is taken up from dietary copper) into the blood. ATP7A also mediates passage of copper across the blood-cerebrospinal fluid (CSF) barrier and the blood-brain barrier. In Menkes disease and occipital horn syndrome (OHS), ATP7A activity is reduced or absent and copper export from the enterocytes is impaired (Kaler, *Nat. Rev. Neurol.* 7:15-29, 2011). As a result, copper accumulates in intestinal cells and less copper is delivered to the blood, resulting in restricted copper supply to other tissues, particularly the brain. A hereditary distal motor neuropathy associated with ATP7A mutations (ATP7A-related distal motor neuropathy; also known as spinal muscular atrophy, distal, X-linked 3 (SMAX3)) has also been recently identified (Kennerson et al., *J. Hum. Genet.* 86:343-352, 2009). This adult-onset disorder is not associated with decreased serum copper levels, unlike Menkes disease and OHS.

SUMMARY

Provided herein are codon-optimized ATP7A nucleic acid molecules, specifically codon-optimized nucleic acids encoding a reduced-size ATP7A protein, and vectors and recombinant viruses including the codon-optimized ATP7A nucleic acids. These nucleic acids can be used in methods for the treatment of copper transport disorders, such as Menkes disease, occipital horn syndrome, or ATP7A-related distal motor neuropathy.

In some embodiments, isolated codon-optimized nucleic acid molecules encoding a reduced size ATP7A protein are disclosed herein. In some examples, the nucleic acid molecules include a nucleic acid with at least 90% sequence identity to the nucleotide sequence of SEQ ID NO: 1. In particular examples, the nucleic acid molecule has the sequence of SEQ ID NO: 1 or encodes the amino acid sequence of SEQ ID NO: 2.

Also disclosed herein are vectors, such as adeno-associated virus (AAV) vectors, that include the disclosed codon-optimized nucleic acid molecules encoding reduced-size human APT7A. In some examples, the vectors further comprise a promoter, such as a β-actin promoter. In additional examples, the vectors further comprise an enhancer, such as a cytomegalovirus enhancer. Recombinant viruses (such as recombinant AAV (rAAV)) including the codon-optimized nucleic acid molecules encoding reduced-size human ATP7A are also disclosed herein. Further provided are isolated host cells comprising the nucleic acid molecules or vectors disclosed herein. For example, the isolated host cells can be cells suitable for propagation of rAAV. Compositions including the disclosed nucleic acid molecules, vectors and viruses are also disclosed herein.

Disclosed herein are methods of treating a subject diagnosed with an ATP7A-related copper transport disorder (such as Menkes disease, OHS, or ATP7A-related distal motor neuropathy). In some embodiments, the methods include administering to the subject an effective amount of a disclosed vector or recombinant virus including a codon-optimized nucleic acid molecule encoding a reduced-size human ATP7A, or compositions including the vector or virus. In some examples, the methods further include administering copper therapy (such as copper histidinate, copper chloride, copper sulfate, or copper gluconate) to the subject. In other embodiments, the methods include treating a subject with Menkes disease by administering to the subject an effective amount of a vector comprising an isolated codon-optimized nucleic acid molecule encoding a reduced-size ATP7A protein operably linked to a promoter and administering copper to the subject. In some examples, the vector or virus is administered to the subject enterally or parenterally, intrathecally, or intracranially into the cerebrospinal fluid or brain.

The foregoing and other features of the disclosure will become more apparent from the following detailed description, which proceeds with reference to the accompanying figures.

BRIEF DESCRIPTION OF THE FIGURES

Figure 2A:
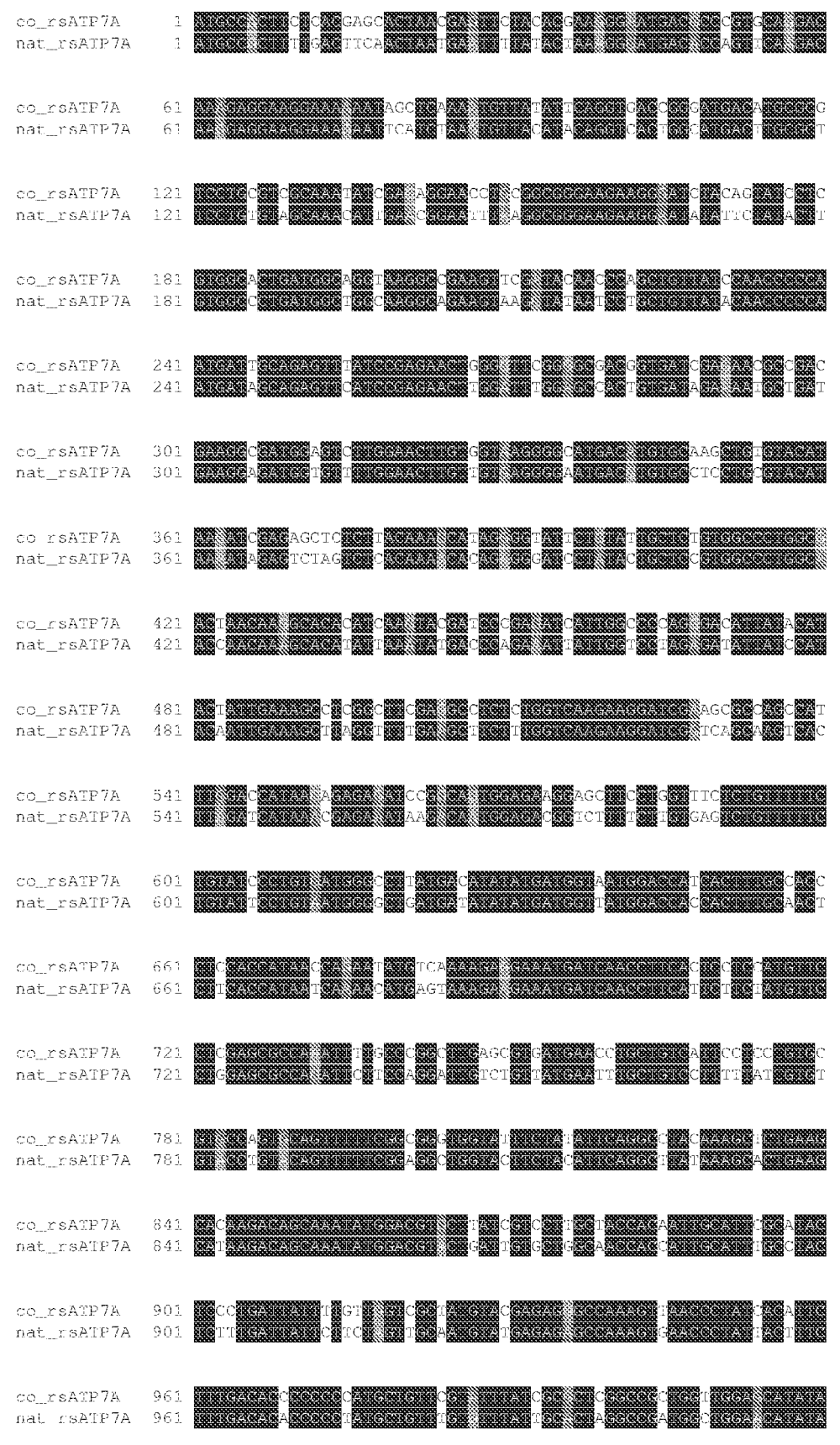
Figure 2B:
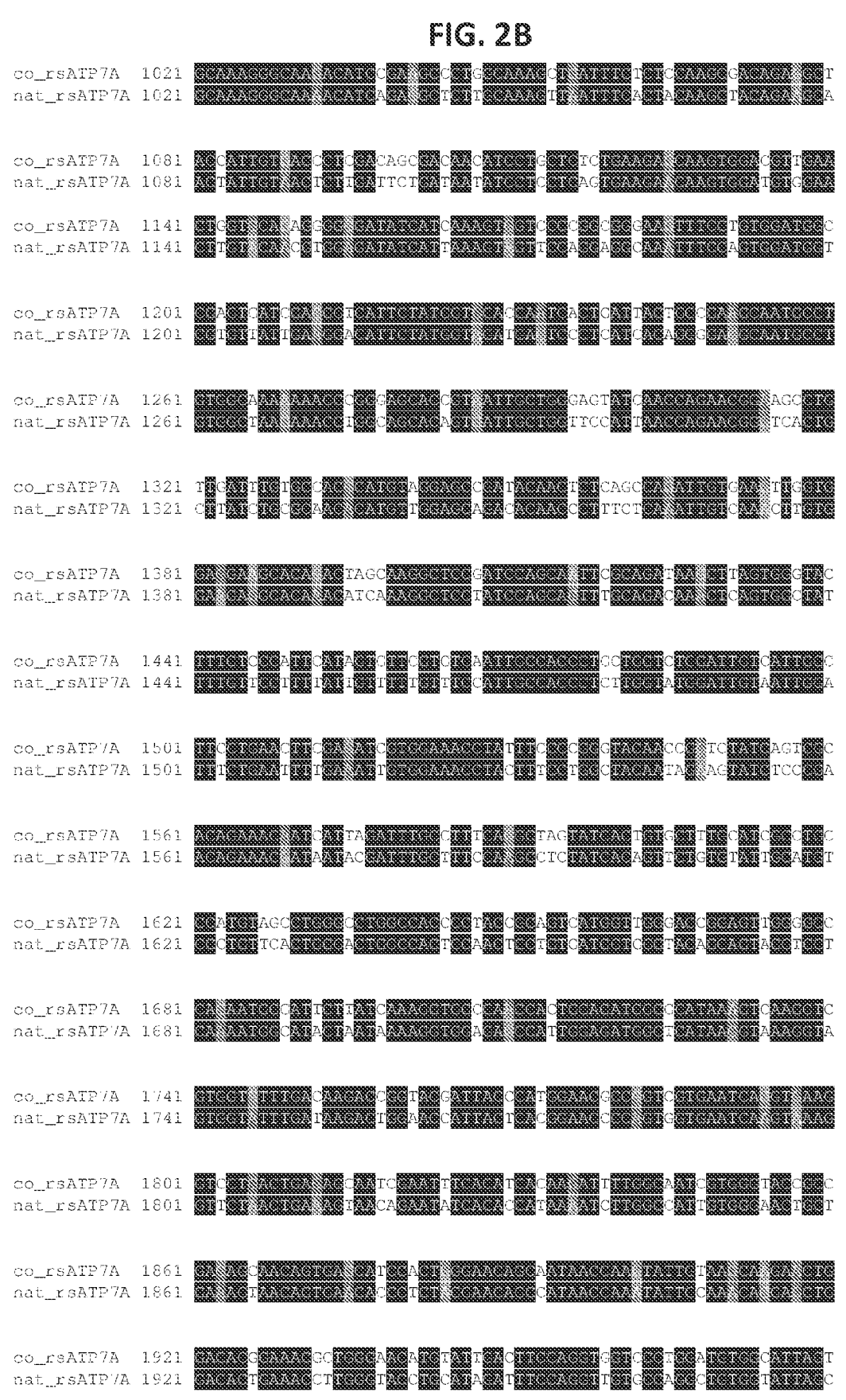
Figure 2C:
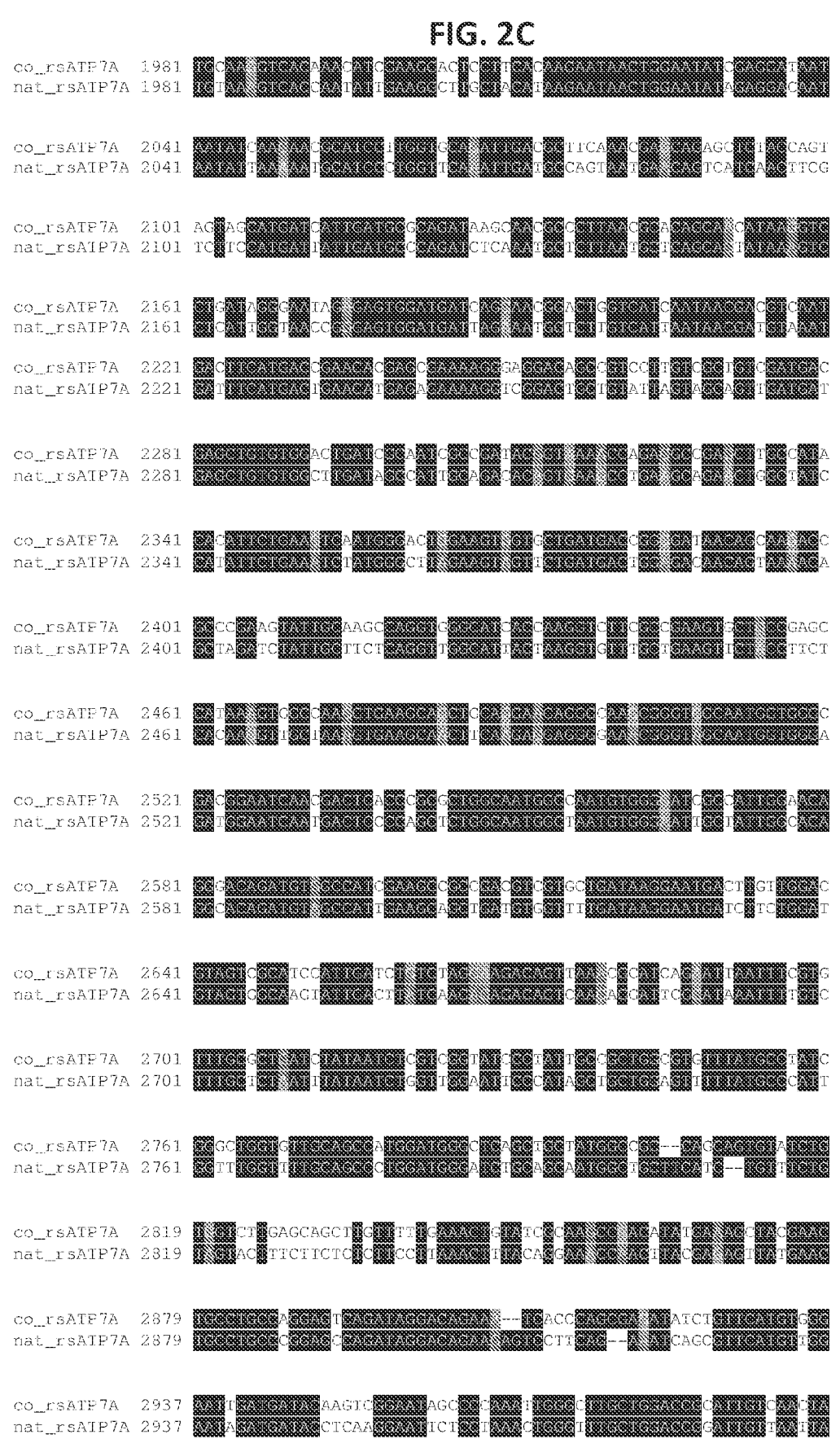

FIGS. 2A-2D show a sequence alignment of the codon-optimized reduced-size human ATP7A nucleic acid sequence (co_rsATP7A; SEQ ID NO: 1) with the native reduced-size human ATP7A nucleic acid sequence (nat_rsATP7A; SEQ ID NO: 3).

FIG. 3 is a schematic of an exemplary recombinant adeno-associated virus (rAAV) construct including a codon-optimized reduced-size ATP7A (co-rsATP7A) cDNA. ITR: inverted terminal repeat; CMV: cytomegalovirus enhancer; CBA: chicken β-actin promoter; polyA: polyadenylation signal.

FIG. 4 is a digital image of expression of reduced-size ATP7A (rs-ATP7A) and co-rsATP7A in transfected HEK293T cells. Lane 1: mock transfected; Lane 2: pTR-CAG-rsATP7A (25 µg); Lane 3: pTR-CAG-co-rsATP7A (1.25 µg); Lane 4: pTR-CAG-co-rsATP7A (25 µg); beta-actin: protein loading control.

SEQUENCE LISTING

Figure 1:
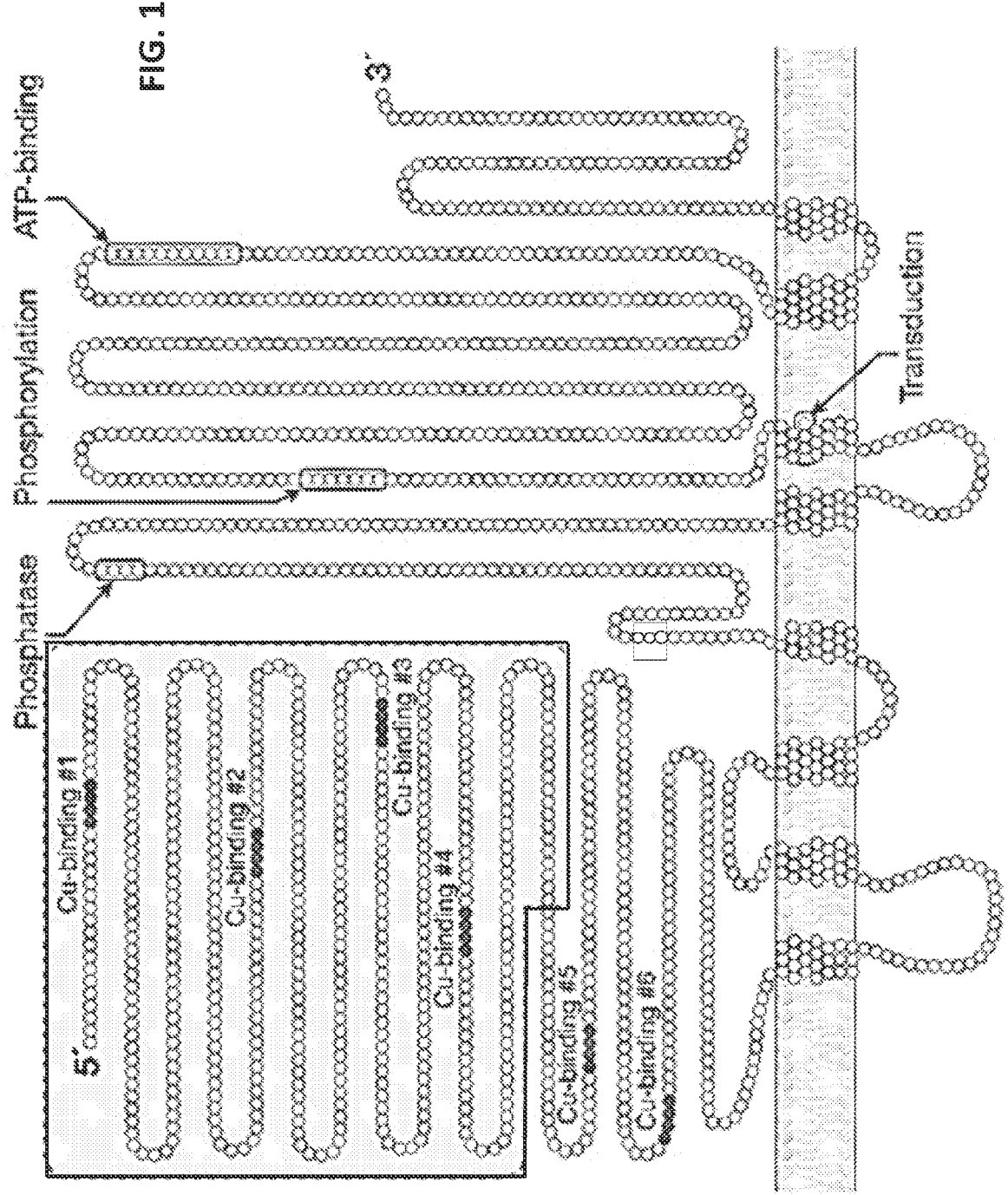
FIG. 1 is a schematic diagram of the human ATP7A protein showing the portion removed (boxed portion) to produce the reduced-size human ATP7A protein. Adapted from Donsante et al., *Mol. Ther.* 19:2114-2123, 2011, incorporated herein by reference in its entirety.

Any nucleic acid and amino acid sequences provided herein or in the accompanying sequence listing are shown using standard letter abbreviations for nucleotide bases and amino acids, as defined in 37 C.F.R. § 1.822. In at least some cases, only one strand of each nucleic acid sequence is shown, but the complementary strand is understood as included by any reference to the displayed strand.

The Sequence Listing is submitted as an ASCII text file in the form of the file named Sequence_Listing.txt, which was created on Mar. 30, 2021, and is 17,860 bytes, which is incorporated by reference herein.

SEQ ID NO: 1 is an exemplary codon-optimized reduced size ATP7A nucleic acid sequence.

SEQ ID NO: 2 is the amino acid sequence of an exemplary reduced size ATP7A protein. SEQ ID NO: 3 is an exemplary native reduced-size ATP7A nucleic acid sequence.

DETAILED DESCRIPTION

I. Terms

Unless otherwise noted, technical terms are used according to conventional usage. Definitions of common terms in molecular biology may be found in Lewin's Genes X, ed. Krebs et al, Jones and Bartlett Publishers, 2009 (ISBN 0763766321); Kendrew et al. (eds.), *The Encyclopedia of Molecular Biology*, published by Blackwell Publishers, 1994 (ISBN 0632021829); Robert A. Meyers (ed.), *Molecular Biology and Biotechnology: a Comprehensive Desk Reference*, published by Wiley, John & Sons, Inc., 1995 (ISBN 0471186341); and George P. Rédei, *Encyclopedic Dictionary of Genetics, Genomics, Proteomics and Informatics*, 3rd Edition, Springer, 2008 (ISBN: 1402067534).

The following explanations of terms and methods are provided to better describe the present disclosure and to guide those of ordinary skill in the art to practice the present disclosure. The singular forms "a," "an," and "the" refer to one or more than one, unless the context clearly dictates otherwise. For example, the term "comprising a nucleic acid molecule" includes single or plural nucleic acid molecules and is considered equivalent to the phrase "comprising at least one nucleic acid molecule." As used herein, "comprises" means "includes." Thus, "comprising A or B," means "including A, B, or A and B," without excluding additional elements.

All publications, patent applications, patents, and other references mentioned herein are incorporated by reference in their entirety for all purposes. All sequences associated with the GenBank Accession Nos. mentioned herein are incorporated by reference in their entirety as were present on Oct. 21, 2015. In case of conflict, the present specification, including explanations of terms, will control.

Although methods and materials similar or equivalent to those described herein can be used to practice or test the disclosed technology, suitable methods and materials are described below. The materials, methods, and examples are illustrative only and not intended to be limiting.

In order to facilitate review of the various embodiments of this disclosure, the following explanations of specific terms are provided:

Adeno-associated virus (AAV): A small, replication-defective, non-enveloped virus that infects humans and some other primate species. AAV is not known to cause disease and elicits a very mild immune response. Gene therapy vectors that utilize AAV can infect both dividing and quiescent cells and can persist in an extrachromosomal state without integrating into the genome of the host cell. These features make AAV an attractive viral vector for gene therapy. There are currently 11 recognized serotypes of AAV (AAV1-11).

ATP7A: ATPase, $Cu^{++}$ transporting, alpha polypeptide. Also known as P-type ATPase copper-transporting ATPase 1. A transmembrane protein involved in transporting copper across membranes. There are two copper-transporting ATPases in humans (ATP7A and ATP7B) which are members of the metal-transporting P-type ATPase family (see, e.g., Lutsenko et al., *Physiol. Rev.* 87:1011-1046, 2007). The ATP7A protein has eight membrane spanning segments. The amino-terminal segment contains six copper binding sites. ATP7A also contains an A-domain, which is required for the phosphatase step of the catalytic cycle and an ATP binding domain consisting of a P domain and an N domain (see FIG. 1).

ATP7A sequences are publicly available. For example, GenBank Accession numbers NC_000023.11 (region 77910656 . . . 78050395) and NC_000086.7 (region 106027276 . . . 106128160) disclose exemplary human and mouse ATP7A genomic nucleic acid sequences, respectively. GenBank Accession numbers NM_000052, NM_001282224, and NR_104109 disclose exemplary human ATP7A cDNA sequences and NP_000043 and NP_001269153 disclose exemplary human ATP7A protein sequences. GenBank Accession numbers NM_009726 and NM_001109757 disclose exemplary mouse Atp7a cDNA sequences and NP_033856 and NP_001103227 disclose exemplary mouse Atp7a protein sequences. All GenBank Accession Nos. described herein are incorporated by reference as present in GenBank on Oct. 21, 2015.

One of ordinary skill in the art can identify ATP7A nucleic acid and protein molecules that vary from those described herein, such as ATP7A sequences having one or more substitutions, deletions, insertions, or combinations thereof, while still retaining ATP7A biological activity (such as copper-transporting activity). In addition, ATP7A molecules include alternatively spliced isoforms and fragments that retain ATP7A biological activity.

ATP7A-related distal motor neuropathy: An adult-onset distal motor neuropathy associated with mutations in ATP7A. The disorder is characterized by progressive distal motor neuropathy and loss of deep tendon reflexes. Foot and hand deformities such as pes *cavus* are typical. Subjects with ATP7A-related distal motor neuropathy do not have low serum copper levels, and do not have hair, skin, or joint abnormalities associated with Menkes disease or OHS.

Codon-optimized: A "codon-optimized" nucleic acid refers to a nucleic acid sequence that has been altered such that the codons are optimal for expression in a particular system (such as a particular species or group of species). For example, a nucleic acid sequence can be optimized for expression in mammalian cells or in a particular mammalian species (such as human cells). Codon optimization does not alter the amino acid sequence of the encoded protein.

Copper Transport Disorders: A disorder caused by a deficiency in copper metabolism, specifically copper transport (e.g., uptake and/or movement of copper by cells). Copper is transported by two copper-transporting ATPases in humans (ATP7A and ATP7B). Copper transport disorders associated with mutations in ATP7A (ATP7A-related copper transport disorders) include Menkes disease, occipital horn syndrome, ATP7A-related distal motor neuropathy. Wilson disease is associated with mutations in ATP7B.

Effective amount: An amount of an agent or composition that alone, or together with a pharmaceutically acceptable carrier or one or more additional agents, induces the desired response. A therapeutic agent or preparation, such as a compound, an isolated nucleic acid, a vector, or a composition containing a nucleic acid or vector, is administered in therapeutically effective amounts. Effective amounts of a therapeutic agent can be determined in many different ways, such as assaying for a reduction in symptoms or improvement of physiological condition of a subject having a disorder (such as a copper transport disorder). Effective amounts also can be determined through various in vitro, in vivo, or in situ assays.

Isolated: An "isolated" biological component (such as a nucleic acid molecule, protein, or virus) has been substantially separated or purified away from other biological components (e.g., other chromosomal and extra-chromosomal DNA and RNA, proteins and/or organelles). Nucleic acids, proteins, and/or viruses that have been "isolated" include nucleic acids, proteins, and viruses purified by standard purification methods. The term also embraces nucleic acids, proteins, and viruses prepared by recombinant expression in a host cell, as well as chemically synthesized nucleic acids or proteins.

The term "isolated" (or purified) does not require absolute purity; rather, it is intended as a relative term. Thus, for example, an isolated or purified nucleic acid, protein, virus, or other active compound is one that is isolated in whole or in part from associated nucleic acids, proteins, and other contaminants. In certain embodiments, the term "substantially purified" refers to a nucleic acid, protein, virus or other active compound that has been isolated from a cell, cell culture medium, or other crude preparation and subjected to fractionation to remove various components of the initial preparation, such as proteins, cellular debris, and other components.

Menkes disease (also known as kinky hair disease or steely hair disease): An infantile onset X-linked recessive neurodegenerative disorder caused by deficiency or dysfunction of the copper-transporting ATPase ATP7A (OMIM 309400). As an X-linked disease, Menkes disease typically occurs in males who appear normal at birth, but present with loss of previously obtained developmental milestones and the onset of hypotonia, seizures and failure to thrive at 2 to 3 months of age. Characteristic physical changes of the hair and facies, in conjunction with typical neurologic findings, often suggest the diagnosis. The scalp hair of infants with classic Menkes disease is short, sparse, coarse, and twisted. Light microscopy of patient hair illustrates pathognomonic pili torti (for example, 180° twisting of the hair shaft) and the hair tends to be lightly pigmented and may demonstrate unusual colors, such as white, silver, or gray. The face of the individual with Menkes disease has pronounced jowls, with sagging cheeks and ears that often appear large. The palate tends to be high-arched, and tooth eruption is delayed. The skin often appears loose and redundant, particularly at the nape of the neck and on the trunk. Neurologically, profound truncal hypotonia with poor head control is almost invariably present. Developmental skills are confined to occasional smiling and babbling in most patients. Growth failure commences shortly after the onset of neurodegeneration and is asymmetric, with linear growth relatively preserved in comparison to weight and head circumference.

The biochemical phenotype in Menkes disease involves (1) low levels of copper in plasma, liver, and brain because of impaired intestinal absorption of copper, (2) reduced activities of numerous copper-dependent enzymes, and (3) paradoxical accumulation of copper in certain tissues (such as the duodenum, kidney, spleen, pancreas, skeletal muscle, and/or placenta). The copper-retention phenotype is also evident in cultured fibroblasts and lymphoblasts, in which reduced egress of radiolabeled copper is demonstrable in pulse-chase experiments.

Mouse models of Menkes disease are available and include the mottled mouse (Mercer, *Am. J. Clin. Nutr.* 76: 1022S-1028S, 1998; for example, brindled (mo-br), tortoise, dappled, viable-brindled, and/or blotchy (mo-blo) mice) and the macular mouse (e.g. Kodama et al., *J. Histochem. Cytochem.* 41:1529-1535, 1993).

Occipital horn syndrome (OHS): A milder allelic variant of Menkes disease (OMIM 304150). Serum copper levels are typically slightly below normal levels in OHS patients. OHS is characterized by wedge-shaped calcifications that form at the sites of attachment of the trapezius muscle and the sternocleidomastoideole to the occiput ("occipital horns"), which may be clinically palpable and/or visible on radiography. The phenotype of OHS includes slight generalized muscle weakness and dysautonomia (syncope, orthostatic hypotension, and chronic diarrhea). Subjects with OHS also typically have lax skin and joints, bladder diverticula, inguinal hernia, and vascular tortuosity. Intellect is usually normal or slightly reduced.

Pharmaceutically acceptable carrier: Pharmaceutically acceptable carriers (vehicles) useful in this disclosure are conventional. *Remington: The Science and Practice of Pharmacy*, The University of the Sciences in Philadelphia, Editor, Lippincott, Williams, & Wilkins, Philadelphia, PA, $21^{st}$ Edition (2005), describes compositions and formulations suitable for pharmaceutical delivery of one or more therapeutic compounds, molecules or agents.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (for example, powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Parenteral administration: Administration of a substance (such as a composition or therapeutic compound) by a route other than through the gastrointestinal tract. Exemplary routes of parenteral administration include intravenous, subcutaneous, intramuscular, intracerebral, intracerebroventricular (e.g., into a cerebral ventricle), intrathecal (e.g., into the spinal canal or cerebrospinal fluid), topical, transdermal, or by inhalation. A skilled clinician can select an appropriate route of administration based on the condition being treated and the treatment being administered.

Promoter: A region of DNA that directs/initiates transcription of a nucleic acid (e.g. a gene). A promoter includes necessary nucleic acid sequences near the start site of transcription. Typically, promoters are located near the genes they transcribe. A promoter also optionally includes distal enhancer or repressor elements which can be located as much as several thousand base pairs from the start site of transcription.

In particular examples, a promoter is "operably linked" to a nucleic acid, such that the promoter and the nucleic acid (such as a codon-optimized rsATP7A nucleic acid disclosed herein) are placed in a functional relationship. For instance, a promoter is operably linked to a coding sequence if the promoter affects the transcription or expression of the coding sequence. Generally, operably linked DNA sequences are contiguous and, where necessary to join two protein-coding regions, in the same reading frame.

Recombinant: A recombinant nucleic acid molecule is one that includes a sequence that is not naturally occurring (such as a codon-optimized sequence) or has a sequence that is made by an artificial combination of two otherwise separated segments of sequence. This artificial combination can be accomplished by chemical synthesis or by the artificial manipulation of isolated segments of nucleic acid molecules, such as by genetic engineering techniques.

Similarly, a recombinant virus is a virus with a nucleic acid sequence that is non-naturally occurring (such as a heterologous sequence that is not from the virus) or made by artificial combination of at least two sequences of different origin. The term "recombinant" also includes nucleic acids, proteins and viruses that have been altered solely by addition, substitution, or deletion of a portion of a natural nucleic acid molecule, protein or virus. As used herein, "recombinant AAV" (rAAV) refers to an AAV particle in which a heterologous nucleic acid molecule (such as a nucleic acid molecule encoding a codon-optimized ATP7A protein) has been packaged.

Vector: A nucleic acid molecule allowing insertion of foreign nucleic acid without disrupting the ability of the vector to replicate and/or integrate in a host cell. A vector can include nucleic acid sequences that permit it to replicate in a host cell, such as an origin of replication. A vector can also include one or more selectable marker genes and other genetic elements. An expression vector is a vector that contains the necessary regulatory sequences to allow transcription and translation of inserted gene or genes. In some non-limiting examples, the vector is an AAV.

II. Codon-Optimized ATP7A, Vectors, and Recombinant Adeno-Associated Viruses

Disclosed herein are nucleic acids encoding a reduced-size ATP7A protein that have been codon-optimized for expression in human cells. In some embodiments, a codon-optimized nucleic acid encoding a reduced-size ATP7A protein includes a nucleic acid that is less than about 5 kb in length (for example, less than about 4.5 kb, less than about 4 kb, less than about 3.5 kb, or less than about 3 kb) encoding an ATP7A protein, wherein the encoded protein retains at least one activity of a native ATP7A protein, including copper binding, copper transport, and/or ATPase activity. In some examples, the encoded ATP7A protein lacks one or more of the six N-terminal copper binding sites (for example, lacks 1, 2, 3, 4, or 5 copper binding sites). In particular examples, the encoded ATP7A protein has two N-terminal copper binding sites (for example, begins after the fourth N-terminal copper binding sites). In some examples, the reduced size APT7A protein begins with a methionine residue present in the native (full-length) protein, while in other examples, the nucleic acid encoding the reduced-size ATP7A protein includes an exogenous translation start site. In a particular example, the codon-optimized reduced-size ATP7A nucleic acid encodes a protein beginning at amino acid number 461 (methionine) of the native ATP7A protein. In one specific example, the nucleic acid encoding the reduced-size ATP7A protein is about 3.1 kb in length. An exemplary codon-optimized reduced-size ATP7A nucleic acid is set forth as SEQ ID NO: 1. In some examples, the codon-optimized nucleic acid encodes a reduced-size ATP7A protein having an amino acid sequence set forth as SEQ ID NO: 2.

In other examples, the codon-optimized nucleic acids have a nucleic acid sequence at least 80%, at least 85%, at least 90%, at least 95%, at least 96%, at least 97%, at least 98% or at least 99% identical to SEQ ID NO: 1. The disclosed codon-optimized nucleic acids encode an amino acid sequence at least 80%, at least 85%, at least 90%, at least 95%, at least 96%, at least 97%, at least 98% or at least 99% identical to SEQ ID NO: 2, wherein the encoded protein retains at least one activity of a native ATP7A protein, including copper binding, copper transport, and/or ATPase activity.

The nucleic acid sequence encoding the reduced-size ATP7A protein disclosed herein is codon-optimized for the cell in which it is to be expressed. Codon usage bias, the use of synonymous codons at unequal frequencies, is ubiquitous among genetic systems (Ikemura, *J. Mol. Biol.* 146:1-21, 1981; Ikemura, *J. Mol. Biol.* 158:573-97, 1982). The strength and direction of codon usage bias is related to genomic G+C content and the relative abundance of different isoaccepting tRNAs (Akashi, *Curr. Opin. Genet. Dev.* 11:660-666, 2001; Duret, *Curr. Opin. Genet. Dev.* 12:640-9, 2002; Osawa et al., *Microbiol. Rev.* 56:229-264, 1992). Codon usage can affect the efficiency of gene expression. Codon-optimization refers to replacement of at least one codon (such as at least 5 codons, at least 10 codons, at least 25 codons, at least 50 codons, at least 75 codons, at least 100 codons or more) in a nucleic acid sequence with a synonymous codon (one that codes for the same amino acid) more frequently used (preferred) in the organism. Each organism has a particular codon usage bias for each amino acid, which can be determined from publicly available codon usage tables (for example see Nakamura et al., *Nucleic Acids Res.* 28:292, 2000 and references cited therein). For example, a codon usage database is available on the World Wide Web at kazusa.or.jp/codon. One of skill in the art can modify a nucleic acid encoding a particular amino acid sequence, such that it encodes the same amino acid sequence, while being optimized for expression in a particular cell type (such as a human cell). In some examples, a codon-optimized ATP7A sequence is generated using software, such as codon-optimization tools available from Integrated DNA Technologies (Coralville, IA, available on the World Wide Web at idtdna.com/CodonOpt), GenScript (Piscataway, NJ), or Entelechon (Eurofins Genomics, Ebersberg, Germany, available on the World Wide Web at entelechon.com/2008/10/back-translation-tool/).

Also disclosed herein are vectors including the codon-optimized nucleic acids encoding the reduced-size APT7A protein. In some examples, vector includes a codon-optimized reduced-size ATP7A nucleic acid operably linked to a promoter. In one non-limiting example, the promoter is a β-actin promoter, such as a chicken β-actin promoter. In other non-limiting examples, the promoter is an ATP7A promoter (such as a human ATP7A promoter), a latency-associated transcript (LAT) promoter from HSV-1, a neuron-specific enolase promoter, or a β-glucuronidase promoter (see, e.g., Husain et al., *Gene Ther.* 16:927-932. 2009). One of skill in the art can select additional promoters that can be used in the disclosed vectors. In additional examples, the ATP7A nucleic acid is also operably linked to an enhancer element (such as a CMV enhancer) and/or a polyadenylation signal (such as a β-globin polyadenylation signal or an SV40 polyadenylation signal).

In some embodiments, the vector is an adeno-associated virus (AAV) vector, an adenovirus vector, an alphavirus vector, a herpesvirus vector, a lentivirus vector, or a vaccinia virus vector. One of skill in the art can select an appropriate vector, for example, for use in the methods described herein.

In particular embodiments, the vector is an AAV vector. The AAV serotype can be any suitable serotype for delivery of transgenes to a subject. In some examples, the AAV vector is a serotype 9 AAV (AAV9). In other examples, the AAV vector is a serotype 5 AAV (AAV5). In other examples the AAV vector is a serotype 1, 2, 3, 4, 6, 7, 8, 10, 11 or 12 vector (i.e. AAV1, AAV2, AAV3, AAV4, AAV6, AAV7, AAV8, AAV10, AAV11 or AAV12). In yet other examples, the AAV vector is a hybrid of two or more AAV serotypes (such as, but not limited to AAV2/1, AAV2/7, AAV2/8 or AAV2/9). The selection of AAV serotype will depend in part on the cell type(s) that are targeted for gene therapy. For treatment of ATP7A-related copper transport disorders, neurons (such as central nervous system neurons or motor neurons) are examples of relevant target cells. In other examples, renal tubule epithelial cells, enterocytes, skin cells, and/or muscle cells are also relevant target cells.

AAV is a small, non-enveloped helper-dependent parvovirus classified in genus Dependoparvovirus of family Parvoviridae. AAV has a linear, single-stranded DNA genome of about 4.7 kb. The genome is flanked by inverted terminal repeats (ITRs) flanking two open reading frames (ORFs), rep and cap. The rep ORF encodes four replication proteins (Rep78, Rep68, Rep52, and Rep4) and the cup ORF encodes three viral capsid proteins (VP1, VP2, and VP3) and an assembly activating protein (AAP). AAV requires a helper virus (such as adenovirus, herpes simplex virus, or other viruses) to complete its life cycle. AAV is currently in use in numerous gene therapy clinical trials worldwide. Although AAV infects humans and some other primate species, it is not known to cause disease and elicits a very mild immune response. Gene therapy vectors that utilize AAV can infect both dividing and quiescent cells and persist in an extrachromosomal state without integrating into the genome of the host cell. AAV possesses several desirable features for a gene therapy vector, including the ability to bind and enter target cells, enter the nucleus, the ability to be expressed in the nucleus for a prolonged period of time, and low toxicity. Because of the advantageous features of AAV, in some embodiments the present disclosure contemplates the use of AAV for the recombinant nucleic acid molecules and methods disclosed herein.

The ITRs are the only component required for successful packaging of a heterologous protein in an AAV capsid. Thus, disclosed herein are AAV vectors that include a codon-optimized nucleic acid encoding a reduced-size ATP7A protein (such as SEQ ID NO: 1) operably linked to a promoter. In some examples, the AAV vector includes 5' and 3' ITRs flanking a codon-optimized nucleic acid encoding a reduced-size ATP7A protein (such as SEQ ID NO: 1) operably linked to a promoter. In one specific example, the flanking ITRs are from AAV2.

The vector may also include additional elements, such as an enhancer element (e.g., a nucleic acid sequence that increases the rate of transcription by increasing the activity of a promoter) and/or a polyadenylation signal. In particular examples, the enhancer is a cytomegalovirus (CMV) enhancer or a woodchuck post-transcriptional regulatory element (WPRE). Exemplary promoters include a chicken β-actin (CBA) promoter, a ubiquitous promoter (such as a glucuronidase beta (GUSB) promoter), or a neuronal-specific promoter (such as platelet-derived growth factor B chain (PDGF-beta) promoter or neuron-specific enolase (NSE) promoter). In additional examples, the polyadenylation signal is a β-globin polyadenylation signal, an SV40 polyadenylation signal, or a bovine growth hormone polyadenylation signal. Other elements that optionally can be included in the vector include tags (such as 6×His, HA, or other tags for protein detection). Any combination of ITRs, enhancers, promoters, polyadenylation signals, and/or other elements can be used in the vectors disclosed herein.

In some examples, the vector includes (from 5' to 3'): an AAV 5'ITR, an enhancer, a promoter, a codon-optimized reduced size ATP7A coding sequence, a polyadenylation signal, and an AAV 3' ITR. In one non-limiting example, the vector includes (from 5' to 3') AAV2 5' ITR, a CMV enhancer, a chicken β-actin promoter, SEQ ID NO: 1 (or a sequence with at least 80% identity to SEQ ID NO: 1), rabbit β-globin polyadenylation signal, and AAV2 3' ITR (e.g., FIG. 3).

There are at least 10 different AAV serotypes (AAV1 through AAV10), which have different tissue or cell tropism. For example, capsid proteins from AAV serotypes 1, 5, and 6 bind to N-linked sialic acid, AAV4 binds to O-linked sialic acid, AAV2, 3, and 6 bind heparin sulfate proteoglycans, and AAV9 binds to N-terminal galactose residues. See, e.g., Murlidharan et al., *Front. Mol. Neurosci.* 7:76, 2014. Thus, specific AAV serotypes may be particularly suitable for transducing specific cell types, such as neurons. In non-limiting examples, AAV serotype 2, AAV serotype 5, or AAV serotype 9 are utilized for central nervous system (CNS) expression with the recombinant nucleic acids, vectors, and methods described herein. One of skill in the art will appreciate that other AAV serotypes can also be utilized in the constructs and methods disclosed herein.

Methods for producing recombinant AAV (rAAV), for example, rAAV suitable for gene therapy are well known in the art, and can be utilized with the recombinant nucleic acid molecules, vectors and methods disclosed herein. In some examples, rAAV is produced using a three plasmid system with a plasmid (vector) including the AAV ITRs flanking a promoter operably linked to a nucleic acid encoding a protein of interest (such as a codon-optimized rsATP7A-encoding nucleic acid), a plasmid including AAV rep and cup genes operably linked to promoters, and a plasmid encoding helper virus proteins. Cells are cotransfected with the three plasmids and viral assembly occurs. The resulting rAAV particles are purified (for example by gradient centrifugation or HPLC) and can be administered to a subject (such as a subject with ATP7A-related copper transport disorder) or are used for transduction of target cells for production of the protein of interest (such as rsATP7A). In other examples, a two plasmid system is utilized, with a packaging plasmid (for example including rep and/or cup genes) and a plasmid including the AAV ITRs flanking a promoter operably linked to a nucleic acid encoding a protein of interest (such as a codon-optimized rsATP7A-encoding nucleic acid). In this case, additional factors for rAAV production are provided by infection with a helper virus. See, e.g., U.S. Patent Application Publication Nos. 2012/0100606, 2012/0135515, 2011/0229971, and 2013/0225666. In particular examples, the rAAV is serotype AAV9 or serotype AAV5.

Also provided herein are isolated host cells comprising the nucleic acid molecules or vectors disclosed herein. For example, the isolated host cell can be a cell (or cell line) appropriate for production of rAAV. In some examples, the host cell is a mammalian cell, such as a HEK-293 (or HEK293T), BHK, Vero, RD, HT-1080, A549, COS-7, ARPE-19, or MRC-5 cell. One of ordinary skill in the art can select additional cells that can be transformed with the nucleic acids and/or vectors disclosed herein.

III. Methods and Compositions for Treating Copper Transport Disorders

Disclosed herein are methods of treating a subject with an ATP7A-related copper transport disorder which include administering to the subject an effective amount of a vector comprising a codon-optimized reduced-size ATP7A nucleic acid or a recombinant virus (such as an rAAV) including a codon-optimized reduced-size ATP7A nucleic acid. In particular examples, a composition including the recombinant virus (e.g., a recombinant virus and a pharmaceutically acceptable carrier) is administered to the subject. The composition can be administered as a single dose or multiple doses (such as 2, 3, 4, or more doses).

Compositions including a vector or virus (such as an rAAV) disclosed herein and a pharmaceutically acceptable carrier are also provided by the present disclosure. Pharmaceutically acceptable carriers are determined in part by the particular composition being administered, as well as by the particular method used to administer the composition. See, e.g., *Remington: The Science and Practice of Pharmacy*, The University of the Sciences in Philadelphia, Editor, Lippincott, Williams, & Wilkins, Philadelphia, PA, 21$^{st}$ Edition (2005). Accordingly, there is a wide variety of suitable formulations of pharmaceutical compositions of the present disclosure.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including sorbitol, saline, and buffered media. Parenteral vehicles include sodium chloride solution, Ringer's dextrose, dextrose and sodium chloride, lactated Ringer's, or fixed oils. In particular examples, the compositions disclosed herein include one or more of sorbitol, polyethylene glycol, or propylene glycol (for example at about 0.1% to about 50%, such as about 1-10%, about 1-5%, about 5-40%, or about 10-30% w/v). In another particular example, the compositions disclosed herein includes lactated Ringer's solution.

Intravenous vehicles may also include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like. The compositions may also include detergents, such as TWEEN-20, TWEEN-40, TWEEN-60, or TWEEN-80 (for example at about 0.05-5%, such as about 0.1%-1%, about 0.5-5%, about 0.2-2%, or about 1-5%). In some embodiments, the compositions are formulated for intracerebral or intravenous administration. Suitable pharmaceutical formulations for administration of rAAV can be found, for example, in U.S. Patent Application Publication No. 2012/0219528 (herein incorporated by reference).

The disclosed compositions are administered to a subject having or suspected to have an ATP7A-related copper transport disorder, including but not limited to Menkes disease, occipital horn syndrome, or X-linked distal hereditary motor neuropathy. One of ordinary skill in the art can identify a subject as having an ATP7A-related copper transport disorder based on clinical presentation, serum copper levels (e.g., Menkes disease or OHS), and/or genetic diagnosis (e.g., presence of one or more mutations in the gene encoding ATP7A). See, e.g., Kaler, *Nature Rev. Neurol* 7:15-29, 2011; Kaler, *Handbook Clin. Neurol.* 113:1745-1754, 2013.

In some embodiments, the disclosed compositions (such as compositions including vector(s) and/or virus(es)) are administered to the subject by any effective route, for example, parenterally or enterally. Exemplary routes of administration include by injection (such as intracranial, intracerebral, intrathecal, intracerebroventricular, intravenous, intraperitoneal, subcutaneous, or intradermal injection), oral, enteral, sublingual, transdermal, intranasal, or inhalation routes of administration. In some examples, the compositions are administered by injection in the CNS, such as intracerebral, intracerebroventricular, intrathecal, intracerebrospinal fluid, epidural, or intraparenchymal injection. In some specific examples, the composition is administered by injection in the CSF. In other examples, the compositions are administered intravenously. In particular examples, the route of administration may be selected based on the serotype of the AAV vector or rAAV used. For example, neuronal transduction has been observed following intravenous administration of AAV1, AAV6, AAV8, AAV9, AAVRh.8, and AAVRh.10 (see, e.g., Murlidharan et al., *Front. Mol. Neurosci.* 7:76, 2014). Direct administration of the composition to the CNS may be required if AAV2, AAV4, or AAV5 are utilized.

In some embodiments, a disclosed rAAV is administered at a dose of about $10^4$ to about $10^{14}$ virions (viral particles). In some examples, the rAAV is administered at a dose of about $10^5$ to about $10^{13}$ virions or about $10^8$ to about $10^{12}$ virions. In specific non-limiting examples, the rAAV is administered at a dose of at least about $10^4$, at least about $10^5$, at least about $10^6$, at least about $10^7$, at least about $10^8$, at least about $10^9$, at least about $10^{10}$, at least about $10^{11}$, at least about $10^{12}$, at least about $10^{13}$, or at least about $1 \times 10^{14}$ virions. In other non-limiting examples, the rAAV is administered at a dose of no more than about $10^{10}$, no more than about $10^{11}$, no more than about $10^{12}$, no more than about $10^{13}$, or no more than about $10^{14}$ virions. In additional examples, the rAAV is administered at a dose of about $10^5$ to about $10^{14}$ viral genomes (vg) (such as about $1.6 \times 10^9$ vg, about $5 \times 10^9$ vg, about $1.6 \times 10^{10}$ vg, about $5 \times 10^{10}$ vg, about $1.6 \times 10^{11}$ vg, about $5 \times 10^{11}$ vg, about $1.6 \times 10^{12}$ vg, about $5 \times 10^{12}$ vg, about $1.6 \times 10^{13}$ vg, or about $5 \times 10^{13}$ vg or about $1.6 \times 10^{14}$ vg.

In other embodiments, the rAAV is administered at a dose of about $1 \times 10^{10}$ to about $1 \times 10^{14}$ viral genomes (vg)/kg. In some examples, the rAAV is administered at a dose of about $1 \times 10^{10}$ to about $1 \times 10^{15}$ vg/kg. In specific non-limiting examples, the rAAV is administered at a dose of at least about $1 \times 10^{10}$, at least about $5 \times 10^{10}$, at least about $1 \times 10^{11}$, at least about $5 \times 10^{11}$, at least about $1 \times 10^{12}$, at least about $5 \times 10^{12}$, at least about $1 \times 10^{13}$, at least about $5 \times 10^{13}$, or at least about $1 \times 10^{14}$ vg/kg. In other non-limiting examples, the rAAV is administered at a dose of no more than about $1 \times 10^{10}$, no more than about $5 \times 10^{10}$, no more than about $1\times10^{11}$, no more than about $5\times10^{11}$, no more than about $1\times10^{12}$, no more than about $5\times10^{12}$, no more than about $1\times10^{13}$, no more than about $5\times10^{13}$, or no more than about $1\times10^{14}$ vg/kg. In one non-limiting example, the rAAV is administered at a dose of about $1\times10^{12}$ vg/kg, about $4\times10^{12}$ vg/kg, or about $1\times10^{13}$ vg/kg.

Appropriate doses can be determined by one of skill in the art, for example through routine trials establishing dose-response curves. The rAAV can be administered in a single dose, or in multiple doses (such as 2, 3, 4, 5, 6, 7, 8, 9 or 10 doses) as needed for the desired therapeutic results.

In some subjects with ATP7A-related copper transport disorders (particularly Menkes disease and OHS), treatment may also include administration of copper therapy by a parenteral (e.g., subcutaneous) route (see, e.g., Kaler et al., *N. Eng. J. Med.* 358:605-614, 2008; Kaler J. *Trace Elem. Med. Biol.* 28:427-430, 2014). This additional therapy may be necessary due to defects in copper transport in the gut resulting from ATP7A defects, and leading to low serum copper levels. Thus, in some embodiments, a subject treated with the compositions disclosed herein (for example a subject with reduced serum copper levels, such as a subject having Menkes disease or OHS) is also treated with copper therapy. Copper therapy may not be necessary in subjects with normal or near normal serum copper levels, such as subjects with ATP7A-related distal motor neuropathy; however, a clinician can identify whether copper therapy should be administered in patients with an ATP7A-related copper transport disorder.

The copper used for treatment may be in any form that can be conveniently administered and having an acceptable level of side effects (such as proximal renal tubular damage). In some examples, copper is in the form of copper histidine, copper histidinate, copper gluconate, copper chloride, and/or copper sulfate. In some examples, the copper is cGMP grade copper, such as cGMP grade copper histidinate. Generally a suitable dose is about 250 µg to about 500 µg of copper (such as copper histidinate, copper chloride, or copper sulfate) per day or every other day. However, other higher or lower dosages (or split doses) also could be used, such as from about 50 µg to about 1000 µg (such as about 50 µg to 200 µg, about 100 µg to 500 µg, about 250 µg to 750 µg, or about 500 µg to 1000 µg) per day or every other day, for example, depending on the subject age (e.g., infant, child, or adult) and body weight, route of administration, or other factors considered by a clinician. In some examples, subjects under 12 months of age are administered the copper in two daily doses, while subjects 12 months of age or older are administered the copper in a single daily dose. Copper therapy is administered by one or more parenteral routes, including, but not limited to subcutaneous, intramuscular, or intravenous administration. In one specific example, copper therapy (such as copper histidinate) is administered by subcutaneous injection.

The copper can be administered to the subject prior to, simultaneously, substantially simultaneously, sequentially, or any combination thereof, with the codon-optimized rsATP7A nucleic acids, vectors, recombinant viruses, or compositions described herein. In some examples, at least one dose of copper is administered within 24 hours of administration of the codon-optimized rsATP7A nucleic acid, vectors, recombinant viruses, or compositions described herein. Additional doses of copper can be administered at later times, as selected by a clinician. In some examples, copper therapy is administered daily for at least 3 months, at least 6 months, at least 1 year, at least 2 years, at least 3 years or more (such as about 3 months to 5 years, 6 months to 3 years, 1 to 2 years, 2 to 6 years, or 1 to 5 years). Copper therapy (such as daily administration of copper) may begin immediately upon diagnosis of a subject with an ATP7A-related copper transport disorder and in some examples may occur prior to administration of the codon-optimized rsATP7A nucleic acids, vectors, recombinant viruses, or compositions described herein, and also continue daily following rsATP7A administration. One of ordinary skill in the art can also select additional treatments for subjects with an ATP7A-related copper transport disorder, such as L-threo-dihydroxyphenylserine (L-DOPS, also known as droxidopa).

In some embodiments, the methods also include selecting a subject for treatment with a disclosed codon-optimized reduced size ATP7A nucleic acid, a vector or virus including a codon-optimized reduced size ATP7A nucleic acid, or a composition including such nucleic acids, viruses, or vectors. For example, the disclosed methods can include selecting a subject with an ATP7A-related copper transport disorder, such as Menkes disease, occipital horn disease, or ATP7A-related distal motor neuropathy. Selection of a subject can be based on clinical symptoms, biochemical findings, molecular diagnostics (such as presence of one or more mutations in ATP7A), or a combination of two or more thereof. Thus, in some examples, a subject with an ATP7A-related copper transport disorder is selected based on clinical symptoms, such as coarse hair, hypotonia, seizures, cerebral and cerebellar neurodegeneration, and/or failure to thrive in infants at about 2-3 months of age (e.g., Menkes disease), cutis *laxa*, loose joints, wedge-shaped calcium deposits of the occipital bone, and/or coarse hair (e.g., OHS), or progressive distal motor neuropathy, pes *cavus*, hammer toes, and/or curled fingers (e.g., ATP7A-related distal motor neuropathy). In other examples, the subject is selected based on biochemical findings, such as low serum copper levels, low serum ceruloplasmin levels, and/or abnormal serum or CSF neurochemical levels (such as dopamine, norepinephrine, or metabolites thereof), either alone or in conjunction with clinical symptoms. In other examples, the subject is selected based on abnormal plasma or CSF neurochemical alone, in the absence of any other biochemical or clinical symptoms. Exemplary methods of determining serum copper, serum ceruloplasmin, or serum or CSF neurochemical levels are described below.

In still further examples, a subject with an ATP7A-related copper transport disorder is selected based on molecular diagnostics, for example, presence of one or more mutations in ATP7A, such as those that result in reduced ATP7A activity or absence of detectable ATP7A expression. Subjects may be selected based on ATP7A DNA sequence alone, in the absence of any other biochemical or clinical abnormality or may be selected based on presence of ATP7A mutation(s) and one or more other biochemical and/or clinical symptom. Exemplary mutations in ATP7A include those described in International PCT Publication No. WO 2010/042102, incorporated herein by reference in its entirety, for example, Q197X, R201X, A629P, S637L, G666R, G727R, S833G, G1019D, N1304S, A1362D, IVS8, AS, dup5, EVS9,DS+6T>G, IVS21,DS,+3A>T, Del4246-4260, and Del4284-4315. Additional exemplary ATP7A mutations are described in Kaler, *J. Trace Elem. Med. Biol.* 28:427-430, 2014, incorporated herein by reference in its entirety, and Online Mendelian Inheritance in Man (OMIM) Accession No. 300011, incorporated herein by reference as present in OMIM on Oct. 21, 2015. One of ordinary skill in the art can identify additional ATP7A mutations (including those not yet identified) that may be present in a subject with an ATP7A-related copper transport disorder. Exemplary methods of identifying presence of one or more ATP7A mutations in a subject include sequencing (e.g., genomic or cDNA sequencing), allele-specific PCR or allele-specific oligonucleotide hybridization, microarray analysis, denaturing gradient gel electrophoresis, denaturing HPLC, enzyme mismatch cleavage, or other methods known to one of ordinary skill in the art.

In some embodiments, the effectiveness of treatment of a subject with a codon-optimized reduced-size ATP7A cDNA (such as rAAV containing a codon-optimized reduced-size ATP7A nucleic acid as disclosed herein) is evaluated by determining one or more biochemical marker of copper metabolism in a sample from a subject (such as serum or CSF copper level, serum ceruloplasmin level, plasma or CSF catecholamine levels, or cellular copper egress). Methods of detecting these biochemical markers of copper metabolism are well known in the art.

In some examples, a value for a biochemical marker of copper metabolism (such as copper level, ceruloplasmin level, catecholamine level, or cellular copper egress) in a sample from a subject is compared to a value for the same marker from a control (such as a reference value, a control population, or a control individual). In some examples, a control is a subject with untreated APT7A-related copper transport disorder (or a reference value or a control population with untreated APT7A-related copper transport disorder). In other examples, a control is a healthy subject (such as a subject that does not have a copper transport disorder) or a reference value or healthy control population. In some examples, the control may be samples or values from the subject with the APT7A-related copper transport disorder, for example, prior to commencing treatment.

In some examples, the biochemical marker of copper metabolism in a sample from a subject is compared to a value obtained from a control sample from a single individual. In other examples, the biochemical marker of copper metabolism in a sample from a subject is compared to a value obtained from a control population, such as control samples from more than one individual (such as two or more individuals, five or more individuals, ten or more individuals, or even 100 or more individuals). In the case of a control population, the value of the sample from the subject can be compared to the mean of the control population values or to the range of the values from the control population. In further examples, the biochemical marker of copper metabolism in a sample from a subject is compared to a reference value, such as a standard value obtained from a population of normal individuals that is used by those of skill in the art. Similar to a control population, the value of the sample from the subject can be compared to the mean reference value or to a range of reference values (such as the high and low values in the reference group or the 95% confidence interval).

Copper Levels

One biochemical marker of copper metabolism is the level of copper in a sample from a subject (such as serum, plasma, or CSF). In some examples, reduced copper level as compared to a normal control individual or normal control population is a marker of Menkes disease or OHS. Methods of determining copper levels in a sample (such as serum, plasma, or CSF from a subject) are well known to one of skill in the art. In some examples, methods for determining copper levels in a sample include flame atomic absorption spectrometry, anodic stripping voltammetry, graphite furnace atomic absorption, electrothermal atomic absorption spectrophotometry, inductively coupled plasma-atomic emission spectroscopy, and inductively coupled plasma-mass spectrometry. See, e.g. Evenson and Warren, *Clin. Chem.* 21:619-625, 1975; Weinstock and Uhlemann, *Clin. Chem.* 27:1438-1440, 1981; WO 93/017321.

Ceruloplasmin Levels

Ceruloplasmin is the major copper-carrying protein in the blood. This protein has ferroxidase and amine oxidase activity and catalyzes the enzymatic oxidation of p-phenylenediamine (PPD) and Fe (II). Levels of ceruloplasmin in a sample from a subject (such as serum, plasma, or CSF) are a biochemical marker of copper metabolism. In some examples, reduced ceruloplasmin level as compared to normal control sample or population or a reference value is a marker of Menkes disease or OHS.

Methods of determining ceruloplasmin levels in a sample (such as serum, plasma, or CSF) are well known to one of skill in the art. In one example, ceruloplasmin levels in a sample are determined by measuring ceruloplasmin oxidase activity (such as PPD-oxidase activity or ferroxidase activity). See, e.g., Sunderman and Nomoto, Clin. Chem. 16:903-910, 1970). The rate of formation of oxidation product is proportional to the concentration of serum ceruloplasmin (with a correction for non-enzymatic oxidation of substrate). In another example, ceruloplasmin levels in a sample are determined by immunoassay, such as ELISA, dissociation-enhanced time-resolved fluoroimmunoassay, or turbidimetric immunoassay (see, e.g., U.S. Pat. Nos. 6,806,044; 6,010,903; 5,491,066). In a further example, ceruloplasmin levels are determined by purifying ceruloplasmin and analyzing the copper content using inductively coupled plasma mass spectroscopy to provide a copper ion specific signal; and the sample is evaluated for ceruloplasmin based on the copper ion specific signal (see, e.g., U.S. Pat. Publication No. 2007/0161120).

Catecholamine Levels

Copper is required for activity of metabolic enzymes (such as dopamine β hydroxylase, lysyl oxidase, and cytochrome c oxidase). For example, copper is required for the activity of the enzyme dopamine β hydroxylase (DBH), which converts dopamine to norepinephrine. In some examples, catecholamine levels (such as plasma or CSF catecholamine levels) are correlated with DBH activity. A portion of the metabolic pathway of dopamine and norepinephrine is shown below.

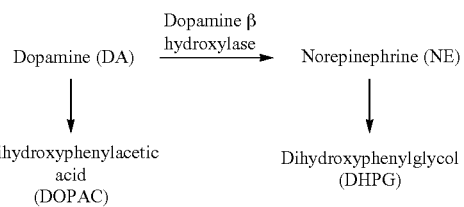

If there is decreased copper available (such as in Menkes disease or OHS), activity of DBH is decreased, resulting in decreased norepinephrine levels and increased dopamine levels. Substrates and metabolites of dopamine (DA) and norepinephrine (NE) are also affected.

Catecholamine levels can be informative to changes in copper metabolism. As the activity of one or more enzymes (such as DBH) change, the ratio of substrate metabolites to product metabolites can indicate the direction of the change. In some examples, increases in enzyme activity will be reflected by decreases in the ratio of one or more substrates to its products. Likewise, decreases in enzyme activity will be reflected by increases in the ratio of one or more substrates to its product (such as the ratio of dopamine to norepinephrine). These ratios can be ratios of two metabolites or ratios of complex relationships among metabolites. Further, the metabolites do not need to be direct product-substrate metabolites of specific enzymes (or a specific enzyme), but can be ratios of any two or more metabolites (such as the ratio of DOPAC:DHPG or DA:NE).

In some examples, the quantity of one or more catecholamines (reported in either an absolute or relative concentration, or a ratio thereof) is correlated to DBH activity. Thus, some of the provided methods involve quantifying one or more catecholamine in a biological sample from a subject. Catecholamines include compounds that include a catechol group (such as the classical catecholamines, for example, dopamine, norepinephrine, and epinephrine). In additional examples, catecholamines include metabolites or substrates of the classical catecholamines. In some examples, catecholamines include metabolites of dopamine (for example, DOPAC, 3-methoxytyramine, and homovanillic acid) and metabolites of norepinephrine (for example, DHPG, normetanephrine, 3,4-dihydroxymandelic acid, 3-methoxy-4-hydroxymandelic acid, and 3-methoxy-4-hydroxyphenylethylene glycol).

Methods of determining catecholamine levels are known to one of skill in the art. These methods include fluorometric, radioenzymatic, immunologic (such as radioimmunoassay), electrophoretic, electrochemical (such as fast scan cyclic voltammetry) and chromatographic (such as high pressure liquid chromatography (HPLC)) methods, or combinations thereof. See, e.g., Raum, *Am. J. Physiol. Endocrinol. Metab.* 247: E4-E12, 1984; Robinson et al., *Clin. Chem.*, 49:1763-1773, 2003; Holmes et al., *J. Chromatogr. B Biomed. Appl.* 653:131-138, 1994; Eisenhofer et al., *Clin. Chem.* 32:2030-2033, 1986. In a particular example, catecholamine levels are determined by high-pressure liquid chromatography with electrochemical detection.

In some examples, catecholamine levels are correlated with DBH activity. In particular examples, catecholamines include dopamine, norepinephrine, dihydroxyphenylacetic acid (DOPAC), dihydroxyphenylglycol (DHPG), or a combination of two or more thereof. For example, patients with ATP7A-related copper transport disorders have decreased DBH activity, which can be reflected by an increase in the substrate of the enzyme (such as dopamine) or an increase in a metabolite of the substrate (such as DOPAC, 3-methoxytyramine, and homovanillic acid) as compared to a healthy subject or population. In other examples, decreased DBH activity can be reflected by a decrease in a product of the enzyme (such as norepinephrine) or a decrease in a metabolite of the product of the enzyme (such as DHPG, normetanephrine, 3,4-dihydroxymandelic acid, 3-methoxy-4-hydroxymandelic acid, and 3-methoxy-4-hydroxyphenylethylene glycol).

In additional examples, a ratio of catecholamine levels correlates with DBH activity. Decreased DBH activity can be reflected by an increase in the ratio of a substrate of the enzyme (such as dopamine) to a product of the enzyme (such as norepinephrine) as compared to a normal control sample or population or a reference value. In other examples, decreased DBH activity is correlated to an increase in the ratio of DOPAC to DHPG.

Cellular Copper Egress

ATP7A is responsible for the transport of copper across the plasma membrane from the cell cytoplasm to the external environment. As a result, cells expressing an ATP7A with reduced or absent copper transport activity accumulate copper inside the cell and exhibit reduced cellular copper egress. In some examples, reduced cellular copper egress can be used as a biochemical marker of abnormal copper metabolism.

Methods for determining cellular copper egress are well known in the art. Classically, egress of radiolabeled copper is measured in pulse-chase experiments utilizing isolated cells (such as isolated fibroblast or lymphoblast cells), such as cells from an individual having Menkes disease or OHS. See, e.g., La Fontaine et al., *J. Biol. Chem.* 273:31375-31380, 1998; Goka et al., *Proc. Natl. Acad. Sci. USA* 73:604-606, 1976. In some examples, cells (such as fibroblast or lymphoblast cells) are incubated with radioisotopic copper (such as 64Cu or 67Cu) and the cells are allowed to take up the copper. Uptake of copper by the cells can be determined by measuring the radioisotope in the cells (such as by scintillation counting). Once the cellular copper is in equilibrium with the extracellular copper, copper egress can be measured (such as loss of copper from the cells in a period of time). In other examples, cells are cultured in standard medium and total intracellular copper is measured in isolated cells, for example by atomic absorption spectroscopy. Cellular copper egress can also be reflected by copper retention of cells. Copper retention is the amount of copper remaining in cells (for example cells labeled with radioisotopic copper) following a period of time in medium lacking the radioisotopic copper.

Example 1

Codon-Optimized Reduced-Size ATP7A

This example describes construction of the codon-optimized reduced-size ATP7A cDNA.

The codon-optimized reduced-size ATP7A sequence was generated from native reduced-size ATP7A sequence (SEQ ID NO: 3) using Codon Optimization software (Integrated DNA Technologies, available at idtdna.com/CodonOpt). Criteria used to select the specific sequence included low complexity, codon fitness, codon usage patterns, and codon context. The sequence of SEQ ID NO: 1 was selected for constructing vectors and further experiments.

Example 2

Production of Codon-Optimized Reduced-Size ATP7A AAV

This example describes construction of AAV containing the codon-optimized reduced-size ATP7A cDNA and expression in HEK293T cells.

The codon-optimized version of rs-ATP7A (co.rsATP7A; SEQ ID NO: 1) was synthesized and cloned into an AAV9 vector containing the CMV/CBA promoter/enhancer elements (FIG. 3). Triple-transfection method was used to produce high-titer AAV9. This method entailed transient transfection of HEK293T cells with three plasmids: one encoding the transgene plus promoter, flanked by internal terminal repeats (ITRs), one encoding the AAV rep and cap genes, and a helper plasmid providing adenoviral protein function. Prior to animal studies, expression of co.rsATP7A in CHO cells and HEK293T cells was assessed. As shown in FIG. 4, transfection of HEK293T cells with pTR-CAG-rsATP7A resulted in low, but detectable amounts of rsATP7A protein (Lane 2, 25 µg total protein loaded). In contrast, transfection with the codon-optimized version (pTR-CAG-co-rsATP7A) resulted in about 40-fold higher gene expression (Lane 3, 1.25 µg total protein loaded, Lane 4, 25 μg total protein loaded) than transfection with the native rsATPA construct (compare Lanes 2 and 4).

Example 3

Co-rsATP7A Enhances Survival in a Mouse Model of Menkes Disease

This example describes survival in a mouse model of Menkes disease when treated with AAV9 co-rsATP7A in combination with copper histidinate.

Figure 5:
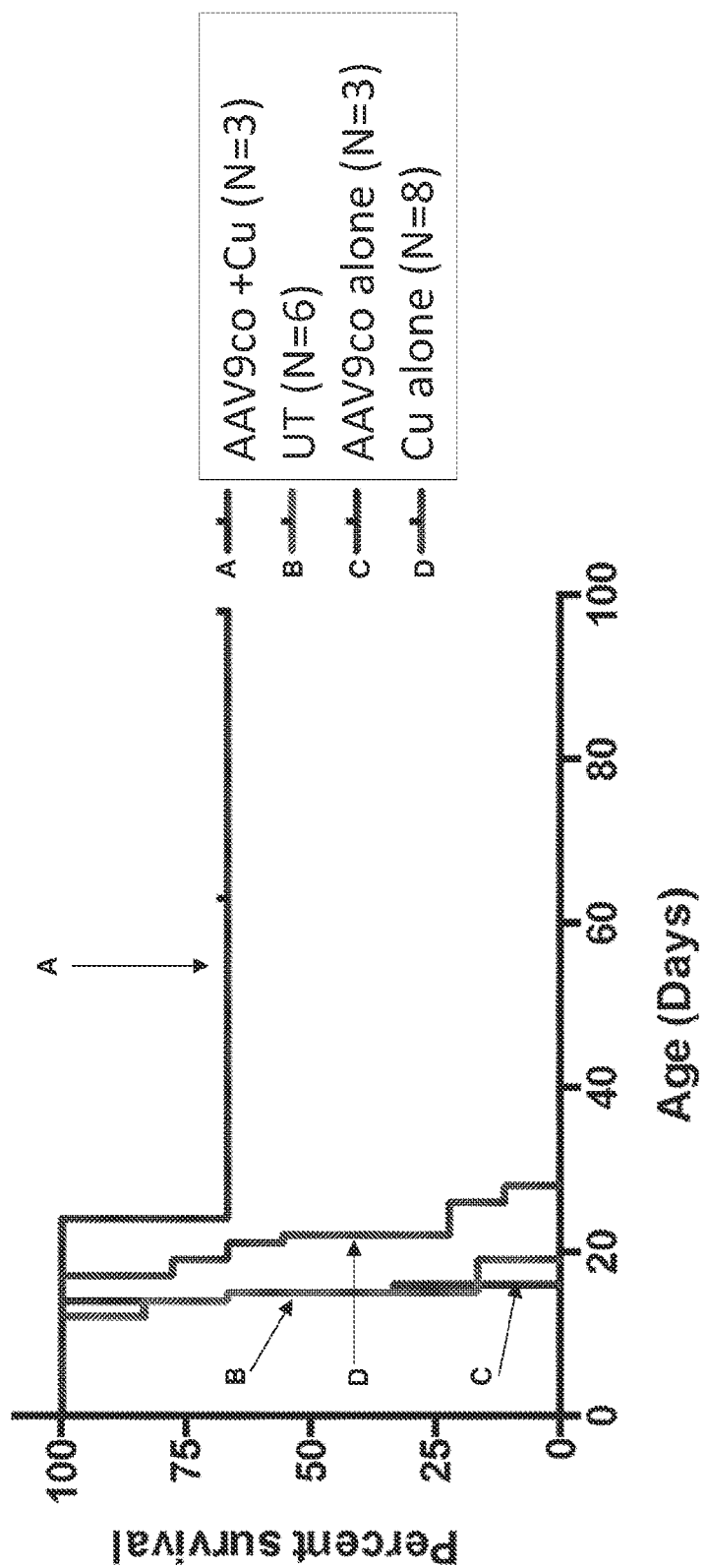
FIG. 5 is a graph showing survival of mo-br mice treated with rAAV9-co-rsATP7A (AAV9) and copper histidinate, untreated (UT), treated with AAV9co alone, or treated with copper histidinate alone.

The AAV9 co-rsATP7A described in Example 2 was administered to C57BL/6-Atp7a$^{mo-br}$ mice (mo-br mice) by intracerebroventricular injection. The mice were injected bilaterally on day two of life with $1.6 \times 10^9$ vg in 5 μl of lactated Ringer's solution. Some of the mice were also treated with copper histidinate (15 μg) by subcutaneous injection during the first week of life (5 μg, d4-6). About 70% of the mice treated with combination AAV9 co-rsATP7A and copper histidinate survived at least 100 days (FIG. 5). In contrast, mice treated with AAV9 alone and untreated mice did not survive past 20 days, and mice treated with copper histidinate did not survive beyond about 28 days (FIG. 5).

Figure 6:
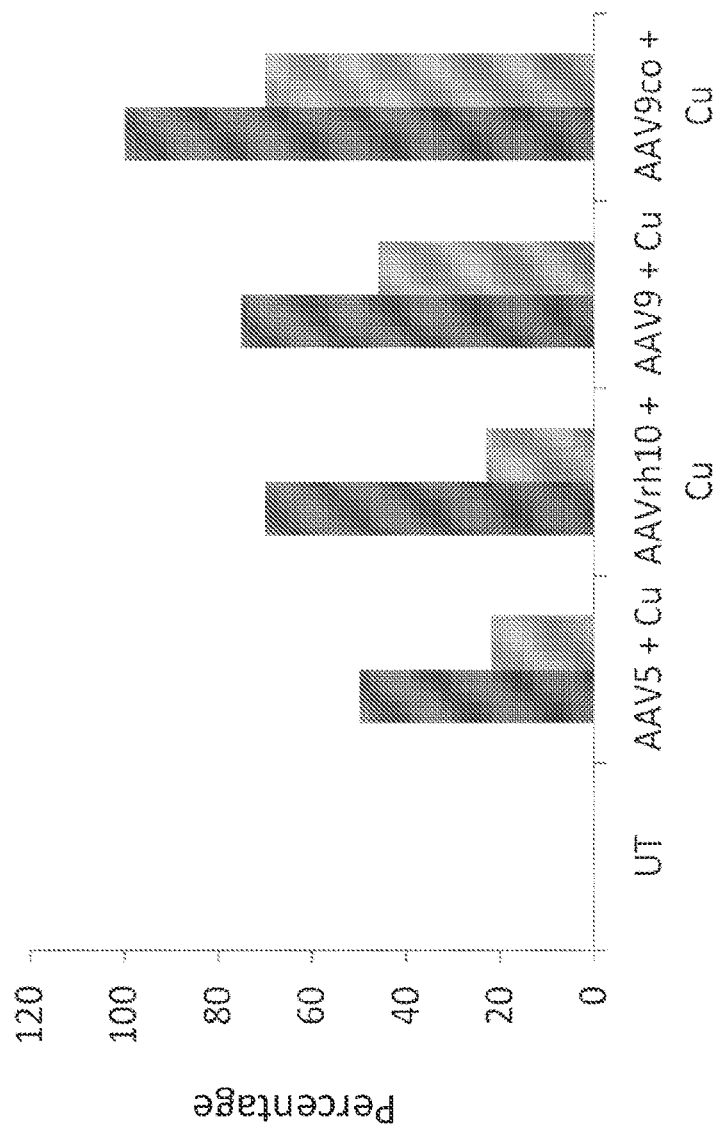
FIG. 6 is a graph showing survival to weaning (dark gray bars) or prolonged survival (light gray bars) in untreated (UT) mice, mice treated with AAV5-rsATP7A and copper histidinate (AAV5+Cu), AAVrh10-rsATP7A and copper histidinate (AAVrh10+copper), AAV9-rsATP7A and copper (AAV9+Cu), and AAV9 co-rsATP7A and copper (AAV9co+Cu). rsATP7A is reduced-size ATP7A cDNA (native sequence (non-codon-optimized)).

Different AAV serotypes were also tested for efficacy in mo-br mice. All showed increased survival compared to untreated mice, which did not survive to weaning (FIG. 6). AAV9 co-rsATP7A showed the highest efficacy, with 100% of the treated mice surviving to weaning and 70% showing long-term survival (FIG. 6).

Example 4

Evaluation of Codon-Optimized Reduced-Size ATP7A in a Mouse Model of Menkes Disease This example describes testing of the efficacy of the codon-optimized reduced-size ATP7A AAV in a mouse model of Menkes Disease.

The AAV described in Example 2 are administered to C57BL/6-Atp7a$^{mo-br}$ mice (mo-br mice) by intracerebroventricular injection. The mice are injected bilaterally on day two of life with specific doses of viral particles (such as those in Table 1) in 2 μl of lactated Ringer's solution. Some mice are also treated with copper histidinate by subcutaneous injection (15 μg total dose) during the first week of life. Wild type mice are used as controls in most cases, since untreated mo-br mice die before weaning.

TABLE 1

Virus and Copper Doses and Timing

| Dose Level | Total Dose (vg) | Dose/kg | scCu dose |
|---|---|---|---|
| Low | $5.0 \times 10^9$ ICV d 2 | $3.3 \times 10^{12}$ | 5 μg, d 4-6 |
| Medium | $1.6 \times 10^{10}$ ICV d 2 | $1.1 \times 10^{13}$ | 5 μg, d 4-6 |
| High | $5.4 \times 10^{10}$ ICV d 2 | $3.6 \times 10^{13}$ | 5 μg, d 4-6 | vg, viral genomes;
ICV, intracerebroventricular;
sc, subcutaneous,
d, day of life Neurobehavioral testing (wire hang test, rotarod test, and/or gait analysis) is carried out on AAV-treated mo-br mice, AAV plus copper-treated mo-br mice, and wild type mice starting at about day 25 of life. In the wire hang test, mice are placed on a wire cage rack about 50 cm above a soft surface. The rack is inverted and the length of time the mouse can hang from the rack is measured (maximum time 60 seconds). The test may be repeated up to three times per session (one minute rest between tests) if the mouse does not complete the full 60 seconds.

In the rotarod test, mice are placed on a 3.5 cm diameter rod. The rod is rotated at 4 r.p.m. and the length of time the mouse remains on the rod is measured (maximum time 60 seconds). The test may be repeated up to three times per session (one minute rest between tests) if the mouse does not complete the full 60 seconds. The mice are acclimated to the rod for four consecutive days (from 21 to 24 days of age) before testing commences.

Appropriate statistical analysis is used to determine if there are statistically significant differences among wild type, AAV-treated, and mock-treated groups for clinical biochemical, and/or pathological outcome methods. Tests may include Kruskal-Wallis non-parametric one-way analysis of variance. Additional tests, such as student's t test or Wilcoxon signed-rank analysis may also be used for pairwise comparisons, as appropriate.

Untreated mo-br mice do not survive past weaning, so survival of treated mice is one indicator of efficacy of AAV or AAV plus copper treatment. It is expected that surviving treated mo-br mice will potentially have at least partially reduced motor or neurological function (e.g., balance and/or coordination) compared to wild type mice. However, in some examples, surviving treated mo-br mice have little or no neurological deficits compared to unaffected littermates.

Example 5

Neuropathology and Biochemistry of AAV-Treated Mice

This example describes the neuropathology and biochemistry of mice treated with the codon-optimized reduced-size ATP7A AAV in a mouse model of Menkes Disease.

Mice are treated as described in Examples 3 and 4. In some examples, untreated mo-br mice are used for comparison at early time points. Neuropathology is evaluated on brain sections by hematoxylin and eosin (H&E) staining, immunohistochemistry, and/or electron microscopy. In some examples, hippocampal neuron death and/or number of Purkinje cells is scored in H&E stained sections. Treatment efficacy (AAV or AAV plus copper) may be indicated by reduced cell death and/or increased numbers of Purkinje cells compared to untreated mo-br mice (for example at day 12 of life), and in some examples may be comparable to wild type mice. In other examples, myelination is evaluated, for example by Luxol fast blue staining. Myelination levels (for example in the corpus callosum) in treated mo-br mice similar to that observed in wild type mice is an indicator of treatment efficacy.

Brain neurochemistry is also evaluated in treated mo-br mice, untreated mo-br mice, and/or wild type mice. Brain copper levels are measured by graphite furnace atomic absorption and confirmed by inductively coupled plasma mass spectrometry, for example as described in Lenn et al. (*Mol. Genet. Metab.* 91:30-36, 2007). Concentrations of brain dihydroxyphenylacetic acid (DOPAC) and dihydroxyphenylglycol (DHPG) are determined by high-performance liquid chromatography with electrochemical detection in supernatant of brain samples homogenized in 5-10 volumes of 0.4 N perchloric acid containing 0.1% EDTA. In some examples, brain copper amounts of at least about 50-75% of wild type and/or DOPAC: DHPG ratios that are decreased compared to untreated mo-br mice are indicators of the effectiveness of the treatment.

Activity of copper-dependent enzymes such as Cu/Zn superoxide dismutase (SOD1) or cytochrome c oxidase (CCO) may also be determined in treated and wild type mice, for example as described in Prohaska (*J. Nutr.* 121: 355-363, 1991). In some examples, CCO activity is increased in treated mo-br mice compared to untreated mo-br mice.

Example 6

Dose-Ranging Toxicity Studies in Rodents

This example describes an exemplary toxicity study of AAV9 co-rsATP7A in Menkes disease mouse model and adult rats.

The initial component of preclinical safety assessment focuses on mo-br mice that survive to weaning in dose-ranging proof-of-concept (POC) studies. Those studies employ research grade rAAV9 vector containing co-rsATP7A with no additional sequence(s) (such as tags or marker genes) incorporated. The toxicology component focuses on histopathological assessments in three mice per group (rAAV-treated mutant survivors, rAAV-treated wild-type, and untreated wild-type) per dose at 1, 3, and 6 months of age. Evaluation for inflammatory responses in brain by immunohistochemistry involves staining with antibodies against glial fibrillary acidic protein (GFAP), CD-4, CD-8, and isolectin B4. Viral genome copies are determined in brain, as well as peripheral organs including liver, kidneys, lung, heart, and spleen to assess viral escape from the CNS.

No large animal models of Menkes disease are known in which to assess the safety and efficacy of rAAV gene therapy. Therefore, a 12-month dose-ranging toxicity study is conducted in wild-type adult male rats (since the target disease is an X-linked recessive trait). For this and subsequent components of the safety assessment, clinical grade rAAV material is used. All essential components of the co-rsATP7A construct used in prior research grade rAAVs are retained and any reporter gene tag (e.g., hemagglutinin) is excised. The new construct is sequenced in its entirety. GMP process-comparable material for rAAV9-co-rsATP7A is obtained from the UPenn Clinical Vector Core Laboratory or the Voyager Therapeutics AAV Vector Production Facility, at least initially.

Designated dose of rAAV9 co-rsATP7A is administered to the left lateral ventricles of adult male Sprague-Dawley rats after ICV catheter placement. Safety evaluation includes clinical observation, body weight, routine blood work, immune response, gross organ pathology, and histopathology. At baseline and at 30, 90, 180, and 360 days after vector administration, complete blood counts (CBC) and serum chemistries are obtained. Serum and CSF neutralizing antibodies against the AAV capsid and ATP7A transgene and T-cell responses pre- and post-treatment are quantitated, using well-established methods (e.g., Martino et al., *Methods Mol. Biol.* 807:259-272, 2011). CSF is obtained by cisterna *magna* sampling under sedation using a method that minimizes the risk of contamination with blood (Pegg et al., *J. Neurosci. Methods* 187:8-12, 2010). Rats are sacrificed at the expected time of peak vector detection (one week) and at later time points (1, 3, 6, and 12 months) to evaluate tissue clearance of vector. Brain, liver, kidneys, lung, heart, spleen, and gonads are analyzed for histopathology, and quantitative PCR is used to analyze the tissues for vector sequences (minimum of three samples per tissue). One sample of each tissue will include a spike of control DNA with a known quantity of vector genomes, as quality control for qPCR. Six rats per group are analyzed (AAV-treated, mock-treated, untreated) per time point.

In the rat toxicology study, statistical assessment of CBC and serum chemistry results will use ANOVA with treatment group (AAV-treated, mock-treated, untreated) as factors, and time as a covariate. Since there are >20 dependent variables, P<0.01 will be used to establish statistically significant differences between treatment and control groups to minimize the chance of rejecting the null hypothesis incorrectly.

Example 7

Toxicity Study in Non-Human Primates

This example describes studies for evaluation of toxicity of AAV9 co-rsATP7A in non-human primates.

Safety, Biodistribution, Immunogenicity, and Potential Genotoxicity of rAAV9-Co-rsATP7A is Evaluated in Male Non-Human Primates (NHP). In this Phase, the Highest Dose Previously Determined to be Safe in Rodents is Scaled Up Based on Estimated NHP Brain Size and CSF Volume. This Adjusted Dose is Administered to the Left Lateral Ventricles of Juvenile (<4 Year Old) Male Rhesus Macaques Using a MRI-Guided Approach to Intraventricular Catheter Placement (Salegio et al., *Adv. Drug Deliv. Rev.* 64:598-604, 2012). Evaluations Occur at Baseline (Less than 2 Weeks Before Surgery) and 3, 7, 15, 30, 60, 90, 180, and 360 Days after Virus Administration. Safety Endpoints Include Body Temperature, Vital Signs, and Weight. Routine Hematology and Mammalian Chemistry Panels are Analyzed, and Serum and CSF Neutralizing Antibodies Against the AAV Capsid and ATP7A Transgene, and T-Cell Response are Quantitated. Lumbar Puncture for CSF Collection is Performed Under Sedation at Baseline and at the 30, 90, 180 and 360 Time Points. Neurobehavioral Assessments are Also Performed at Baseline and Post-Treatment, by Videotaping to Assess and Quantify Normal and Identifiable Abnormal Behaviors.

At necropsy whole NHP brains from vector-infused and mock-treated control animals are obtained as well as samples of liver, lung, kidney, heart, testes, spleen, and biceps muscle for routine histology. A qualified neuropathologist specifically evaluates the rAAV9 co-rsATP7A treated NHP brains for evidence of neuronal death, axonal degeneration, and abnormal glial cell reactivity, under blinded conditions. The distribution of vector DNA in brain cortex, cerebellum, and choroid plexus dissected at time of sacrifice, as well as in peripheral tissues is determined by quantitative PCR under GLP-like conditions. Linear amplification-mediated (LAM)-PCR is performed to evaluate for viral host genome integration in brain and liver (Nowrouzi et al., *Mol. Ther.* 20:1177-1186, 2012).

For statistical analysis of NHP data (general assessment, CBC, blood chemistry), a mixed models analysis is used, with time as a repeated measure. For all dependent variables, the main effects of group (AAV-treated, mock-treated, untreated) and time, as well as the interaction of group and time, are assessed. A main effect of group with P<0.01 is taken as rejection of the null hypothesis that there is no difference between the groups. As with the rat analyses (Example 6), a lower than required P value for significance is used due to the presence of multiple dependent variables. To assess the effects of treatment on brain histopathology, chi-square tests are used to compare the number of animals per group with and without the histopathological characteristic of interest. To assess the impact of treatment on behaviors of the nonhuman primates, a separate analysis of the short-term and long-term effects is performed to increase the possibility of observing an effect in the AAV treatment

Example 8

Treatment of ATP7A-Related Copper Transport Disorder in a Subject

This example describes an exemplary method for the clinical use of AAV vectors containing a codon-optimized reduced size ATP7A cDNA for treatment of an ATP7A-related copper transport disorder. However, one skilled in the art will appreciate that methods that deviate from these specific methods can also be used to successfully treat a subject with ATP7A-related copper transport disorder.

A patient diagnosed with an ATP7A-related copper transport disorder (such as Menkes disease or OHS) is selected for treatment. The patient is administered a therapeutically effective amount of a recombinant AAV expressing reduced-size ATP7A from a codon-optimized sequence such as a recombinant AAV9 comprising SEQ ID NO: 1, as disclosed herein. The recombinant AAV can be administered intracerebrally (e.g., to the lateral ventricles of the brain), intrathecally (e.g., to the cerebrospinal fluid), or intravenously. An appropriate therapeutic dose can be selected by a medical practitioner. In some cases, the therapeutically effective dose is in the range of $1 \times 10^{10}$ to $1 \times 10^{14}$ viral genomes (vg)/kg, such as about $1 \times 10^{12}$-$1 \times 10^{13}$ vg/kg. For example, the starting intrathecal dose (low dose) can be $1.2 \times 10^{12}$ vg/kg body weight, additional possible doses include $4.0 \times 10^{12}$ vg/kg (medium dose), representing a 0.5 log unit higher than the low dose and $1.3 \times 10^{13}$ vg/kg (high dose, 0.5 log unit higher than medium dose), all administered intrathecally to the cerebrospinal fluid. In most instances, the patient is administered a single dose, though multiple doses may also be administered. The subject can be monitored over time (e.g., 2 months to 5 years, or longer) to determine the effectiveness of the treatment, for example by monitoring serum copper levels, CSF neurochemical levels, brain myelination (e.g., determined by magnetic resonance imaging), and/or neurodevelopmental progress (such as gross motor, language, fine motor-adaptive, and personal-social neurodevelopment) in the subject.

In view of the many possible embodiments to which the principles of the disclosure may be applied, it should be recognized that the illustrated embodiments are only examples and should not be taken as limiting the scope of the invention. Rather, the scope of the invention is defined by the following claims. We therefore claim as our invention all that comes within the scope and spirit of these claims.

I claim:

1. A method of treating a subject with Menkes disease, comprising:
    (a) intravenously administering to the subject an effective amount of a composition comprising:
        about $1\times10^{10}$ to about $1\times10^{14}$ viral genomes (vg)/kg of an adeno-associated virus serotype 9 (AAV9) vector comprising a codon-optimized nucleic acid molecule encoding a reduced-size ATP7A protein wherein the codon-optimized nucleic acid consists of SEQ ID NO: 1 and the codon-optimized nucleic acid is operably linked to a promoter; and
        a pharmaceutically acceptable carrier, and
    (b) administering to the subject an effective amount of copper,
wherein the composition and the copper are administered to the subject sequentially, substantially simultaneously, or simultaneously,
    thereby treating the subject with Menkes disease.

2. The method of claim 1, wherein the subject is intravenously administered about $1\times10^{12}$ to about $5\times10^{13}$ viral genomes (vg)/kg of the AAV9 vector.

3. The method of claim 1, wherein the copper is copper chloride, copper gluconate, copper histidine, copper histidinate, or copper sulfate.

4. The method of claim 3, wherein the copper is administered subcutaneously, intramuscularly, or intravenously.

5. The method of claim 1, wherein the subject is human.

6. The method of claim 1, wherein the subject is administered a single dose of the composition comprising the AAV9 vector comprising the codon-optimized nucleic acid molecule encoding a reduced-size ATP7A protein wherein the codon-optimized nucleic acid consists of SEQ ID NO: 1, and the codon-optimized nucleic acid is operably linked to a promoter; and a pharmaceutically acceptable carrier.

7. The method of claim 1, further comprising administering more than one dose of copper to the subject.

8. The method of claim 7, wherein the more than one doses of copper are administered twice daily if the subject is less than 12 months of age or the more than one doses of copper are administered once daily if the subject is more than 12 months of age.

9. The method of claim 1, wherein the promoter comprises a chicken β-actin promoter.

* * * * *